United States Patent [19]
Kolstad et al.

[11] Patent Number: 6,153,773
[45] Date of Patent: Nov. 28, 2000

[54] METHOD FOR PREPARATION OF PURIFIED GLYCERIDES, AND, PRODUCTS

[75] Inventors: Jeffrey J. Kolstad, Wayzata; Richard D. Benson, Long Lake; Scott D. Bloomer, Eden Prairie; Paraskevas Tsobanakis, Inver Grove Heights, all of Minn.

[73] Assignee: Cargill, Incorporated, Minneapolis, Minn.

[21] Appl. No.: 09/343,341

[22] Filed: Jun. 30, 1999

Related U.S. Application Data

[63] Continuation of application No. 08/812,018, Mar. 6, 1997, Pat. No. 5,959,128, which is a continuation-in-part of application No. 08/614,468, Mar. 13, 1996, Pat. No. 5,859,270.

[51] Int. Cl.[7] ........................................................ C11C 1/00
[52] U.S. Cl. ............................................ 554/169; 554/206
[58] Field of Search .................................... 554/169, 206

[56] References Cited

U.S. PATENT DOCUMENTS

| | | |
|---|---|---|
| 2,651,646 | 9/1953 | Goldsmith . |
| 2,682,550 | 6/1954 | Young et al. . |
| 2,727,913 | 12/1955 | Kuhrt et al. . |
| 2,740,799 | 4/1956 | Young et al. . |
| 2,759,954 | 8/1956 | Miller . |
| 3,097,098 | 7/1963 | Allen et al. . |
| 3,669,848 | 6/1972 | Seiden . |
| 4,018,806 | 4/1977 | Wyness et al. . |
| 5,434,280 | 7/1995 | Peter et al. . |

OTHER PUBLICATIONS

Feuge, R. O. et al., "Modification of Vegetable Oils IX. Purification of Technical Monoglycerides," *J. Amer. Oil Chem. Soc.*, 27:117–122, Apr. 1950.

Monick, J. A., et al., "Separation of Monoglycerides, Diglycerides, and Triglycerides by Liquid–Liquid Extraction," *J. Am. Oil Chem. Soc.*, 33:193–197, May 1956.

Zilch, K. T. et al., "Analysis of Fat Acid Oxidation Product by Countercurrent Distribution Methods," *Analytical Chemistry*, 23(5):775–778, May 1951.

*Primary Examiner*—Deborah D. Carr
*Attorney, Agent, or Firm*—Merchant & Gould P.C.

[57] ABSTRACT

A method of preparing purified ester compositions is provided. The process can be utilized to isolate and purify monoglycerides and propylene glycol monoesters, to advantage. It can also be used to isolate preferred diester products. The invention also concerns equipment for conduct of the processes, provision of preferred food additives, and provision of preferred food industry compositions. The process generally involves use of liquid-liquid extractions, to advantage.

13 Claims, 5 Drawing Sheets

METHOD FOR PREPARATION OF PURIFIED GLYCERIDES, AND, PRODUCTS

CROSS-REFERENCE TO RELATED APPLICATION

The present application is a continuation of U.S. application Ser. No. 08/812,018 which was filed with the United States Patent and Trademark Office on Mar. 6, 1997, and which issued as U.S. Pat. No. 5,959,128 on Sep. 28, 1999. U.S. Pat. application Ser. No. 08/812,018 is a contimuation in part application of U.S. application 08/614,468 which was filed with the United States Patent and Trademark Office on Mar. 13, 1996 now U.S. Pat. No. 5,859,270 and which issued as U.S. Pat. No. 08/812,018 and the complete disclosure of U.S. application Ser. No. 08/614,468 are incorporated herein by reference.

FIELD OF THE INVENTION

The present invention relates to ester production and isolation. In one type of application, it particularly concerns methods of isolating purified monoglycerides from crude monoglyceride mixtures. In another, it concerns isolation of purified diglycerides. In preferred applications, liquid-liquid extraction is utilized to advantage. The techniques can also be applied to isolate related materials, such as propylene glycol monoesters and derivatives of monoglycerides.

BACKGROUND

Monoesters such as monoglycerides are widely used food additives, for example as emulsifiers and dough conditioners. In general, such materials comprise esters of fatty acids. The term "monoglyceride" specifically refers to a derivative of glycerol, i.e., a glyceride, in which only one of the three available hydroxy groups of the glycerol moiety is esterified, hence the prefix "mono-". By "esterified" in this context, it is meant that the glycerol moiety forms the alcohol residue of an ester (typically with a fatty acid residue).

In general, crude monoglyceride mixtures are made from reacting naturally occurring triglycerides, often obtained from oil seed processing, with glycerol. Such reactions generate a mixture of monoglycerides, diglycerides and triglycerides. Limitation on monoglyceride production, via this approach, is generally controlled by: (1) solubility of the glycerol in the reaction mixture; (2) the overall equilibria statistics; and, (3) time. Typical commercially available crude monoglyceride mixtures made using this approach include ratios of monoglyceride:diglyceride:triglyceride (by weight) of about 45:45:10; or about 60:35:5, depending on processing conditions used.

In many instances, it is preferred to utilize more purified monoglycerides. That is, crude monoglyceride compositions or mixtures are purified for at least partial isolation of the monoglycerides from the diglycerides and triglycerides. In general, monoglyceride distillation has been the most widely utilized technique for such purifications. Typically the crude monoglyceride mixture is distilled under vacuum, in a short path distillation process. The distillate generally comprises greater than 90% (by weight) monoglycerides. The remainder generally comprises diglyceride. During the process, the monoglycerides are generally heated to at least 200° C.

In other processes, supercritical extractions have been used for isolation of monoglycerides. These generally concern extraction under pressures greater than atmospheric (typically 30–80 atmospheres) and temperatures in excess of 100° C. (typically 110° C. or so). They generally concern extractions with low molecular weight hydrocarbons, such as propane. Such approaches are generally prohibitively expensive, for application on a large scale.

Closely related materials to monoglycerides include propylene glycol monoesters (PGME's). Such materials are generally made from esterifying propylene glycol with naturally occurring oils, i.e., fatty acid mixtures, resulting in a mixture of monoesters and diesters. Generally the monoesters are isolated by distillation. Such materials are also widely utilized as emulsifiers and as dough conditioners in the food industry.

In certain food applications, diglycerides are used. For example, diglycerides may be used as components of shortening and as fat replacers. As a result, in some instances, it is desirable to isolate diglycerides in a purified form, from a crude mixture. Techniques to accomplish this are described herein. Herein the term "diglyceride" refers to a derivative of glycerol in which two of the three available hydroxy groups of the glycerol are esterified; and, the term "triglyceride" refers to a derivative of glycerol in which all three available hydroxy groups are esterified.

SUMMARY

Methods for preparing purified ester compositions from crude ester compositions are provided.

According to one aspect of the present invention, a method is provided for preparing a purified target ester-containing food composition. Herein the term "target ester" is meant to refer to the selected ester or mixture of esters, of a crude mixture of esters, to be isolated for purification. For example, if the crude ester composition comprises a mixture of glycerides and it is desired to isolate monoglycerides, the target ester fraction comprises the monoglycerides fraction or component of the mixture. Herein the term "food composition" in this context, is meant to include any material or component that is in a suitable form to be used as a food additive and/or in the final food product or food mixture.

In general, the method of preparing a purified target ester containing food composition comprises providing crude ester composition which at least includes:

1. at least one target ester; and,
2. at least one contaminating ester.

Herein the term "contaminating ester" is meant to refer to the ester components of the crude ester composition which do not comprise the target ester.

In general, the target ester will be selected from the group consisting of: (a) $C_3$-diol target esters of fatty acids; (b) $C_3$-triol target esters of fatty acids; and, (c) mixtures of the previous two. In typical instances, the target ester will comprise either monoester(s) or diester(s), or mixtures of the two.

The contaminating ester will also typically be selected from: (a) $C_3$-diol contaminating esters of fatty acids; (b) $C_3$-triol contaminating esters of fatty acids; or, (c) mixtures of the two. Typically the contaminating esters will include triesters, and in some instances will also include diesters or monoesters. For example, if the purpose is to isolate purified monoesters from a composition also comprising diesters and triesters, the target ester will comprise the monoester and the mixture of diesters and triesters will comprise the contaminating ester(s). On the other hand, if the intent is to isolate diesters from such a mixture, then the target ester will comprise the diester mixture and the contaminating esters will comprise the triesters (and most likely also the monoesters). Of course in some instances, both a purified monoester stream and a purified diester stream is desired. In such cases each is a target ester (at least relative to the other).

According to the process, the step of extracting the crude ester composition is conducted with an aqueous alcohol phase that is tuned to selectively extract into the extracted phase a first of: (1) the selected target ester(s); and, (2) the selected contaminating ester(s), relative to a second of: (1) the selected target ester(s); and, (2) the selected contaminating ester(s).

Herein the term "selectively extract", when used in this context, means an extraction which results in a higher ratio, by weight, of the selected ester(s) versus the non-selected ester(s) in the extractant phase, relative to the original phase from which extraction occurs. The "selected ester(s)", of course, may be either the target ester(s) or the contaminating ester(s). Thus, a selective extraction in this context is an extraction which, at the same time as extraction, results in some level of purification of the selected target ester(s), with respect to the contaminating esters.

In certain preferred operations, after the extraction, the extractant phase, upon separation, is treated with a crude triglyceride phase. Typically this is a triglyceride wash. The effect will be to purify the extractant phase, by extracting into the triglyceride wash those ester materials preferentially soluble therein. Thus, as a result of the treatment or wash, there is generated a further purified extractant phase and a triglyceride phase. When such is the case, generally the process will include a step of separating the purified extractant phase from the triglyceride phase, the purified extractant phase in some instances including therein the target ester. When such is the case, the target ester can then be separated from the solvent, to form the resulting food composition. This material may then be preferentially introduced into food products, as described hereinbelow.

In alternate applications, the extractant phase from the first extraction will include therein contaminating ester, that may be alternatively used or recycled, and the raffinate phase will include therein the target ester. The target ester, in the raffinate phase, would then be used in food.

The process is typically and preferably used to purify crude monoester compositions including $C_3$-diol or $C_3$-triol monoesters of fatty acids. The term "$C_3$-diol" as used herein is meant to refer to a 3-carbon chain dihydroxy compound, typically wherein each hydroxy group is on a separate carbon. The term "$C_3$-triol" as used herein is meant to refer to a 3-carbon chain trihydroxy compound, typically wherein each hydroxy group is on a separate carbon atom. Typically $C_3$-diol monoesters purified according to the present invention will comprise propylene glycol monoesters; and, $C_3$-triol monoesters purified according to the present invention will comprise monoglycerides. Analogously, the target ester could be a diester of either a $C_3$-diol or a $C_3$-triol, for example a diglyceride mixture.

Typically, crude ester compositions to be purified according to the present invention will comprise crude ester compositions made from reactions of naturally occurring triglycerides, such as palm oil, canola oil, soybean oil, sunflower seed oil, or beef tallow or various fats. The triol monoesters are typically prepared by reacting such naturally occurring oils or fats with glycerol; and, the $C_3$-diol crude monoester (or diester) compositions are generally prepared by reacting naturally occurring triglycerides with propylene glycol. The term "naturally occurring" in this context and in connection with identifying oils or fats, is merely meant to refer to oils, fats or mixtures of oils and/or fats that can be isolated from natural products; for example from crops or animal processing. It is not meant that the materials are in their natural form, but indeed typically will have been isolated through some form of processing. Also, it is not meant by the term "naturally occurring" that the isolation could not have been from a man-made hybrid plant or animal, or genetically altered plant or animal.

It will also be understood that techniques according to the present invention can be utilized in association with oils/fats that have been modified from their natural form in some manner, for example through hydrogenation or various esterifications. Herein the term "oil" is differentiated from the term "fat" in that oils are generally liquid at room temperature and fats are generally solid or semi-solid at room temperature. Both are triglycerides and will generally be treated analogously in processes according to the present invention.

In some applications, the purification includes a step of adding, to the crude monoester composition to be purified, an effective amount of triglyceride(s) to form a primary extraction triglyceride-containing phase. In this context, the term "effective amount" is generally meant to refer to an amount of triglyceride(s) which will facilitate retention of diglyceride(s) in a "primary extraction triglyceride-containing phase" during the extraction. Typically and preferably the amount of triglyceride(s) addition will be about 30 to 200 parts by weight per 100 parts crude monoester, especially when the triglyceride(s) comprises the same triglyceride(s) (or is derived from the same triglyceride) as was used to form the crude monoester composition. Most typically 45 to 100 parts by weight per 100 parts crude monoester will be used.

Alternatively, one can characterize certain processes according to the present invention in terms of the composition of the mixture from which the monoglycerides are extracted. The mixture would generally comprise at least 30%, by weight, triglycerides, as a result of the triglyceride addition to the crude monoglyceride prior to extraction. In general, the composition would comprise a diglyceride content of no greater than about 2 times the monoglyceride content, by weight. This latter would also typically be true of the crude monoglycerides to be processed. Preferably, the mixture from which the extraction of monoglycerides occurs, has a diglyceride presence which is less than the triglyceride presence, by weight, generally as a result of the triglyceride additions to the crude monoglyceride mixture.

For typical applications, to isolate either monoesters or diesters, when triglycerides are added, the amount of triglyceride addition will be such that the result will have, by weight, more triglycerides than diesters, by weight. When the diester is diglyceride, then the result will be more triglycerides than diglycerides by weight. When such an addition of triglycerides is conducted, the effect may be such that the amount of monoester in a composition, when the extraction occurs, is, in some typical applications, as low as about 20% by weight, based on total weight of ester in the crude ester composition. Similarly when such a dilution occurs, the amount of diester, which typically in the crude composition (before dilution by triglyceride addition) purified would be present at a level of at least 25% by weight, may be diluted such that its presence is as low as about 15% by weight, based on total weight of esters in the phase which is extracted.

Typical, preferred, processes according to the present invention comprise a step of extracting the primary extraction triglyceride-containing phase with an alcohol/water extractant. Typically and preferably the alcohol is a low molecular weight ($C_3$ or less) alcohol. Preferably it is an alcohol of a straight chain hydrocarbon compound. Typically it is a monohydroxy compound, most preferably with a terminal —OH group. Most preferably it is ethanol. Most typically, especially when the alcohol is ethanol, the alcohol/water extraction will comprise, by weight, at least 60% alcohol and no more than about 90% alcohol. Also, typically it will contain 10–40%, by weight, water. Most typically it will include about 70–85% alcohol, and 15–30% water, by weight. Such systems will generally be quite selective, for extraction of monoesters from the crude monoester composition, with substantial selectivity relative to extraction of diesters or triesters. Such systems will also generally have a high extraction factor for monoesters, allowing use of relatively low extractant flow rates.

Preferably, after the step of separating, the alcohol/water extractant phase is treated for isolation of monoester composition therefrom. This will typically involve a step of removing the alcohol/water extractant from the extractant phase, for example by distillation of the alcohol/water. Preferably, regardless of the specific technique used, the step of isolating is conducted without a step of distilling the isolated monoester(s).

In certain preferred operations according to the present invention, especially for monoester isolation, the step of providing crude monoester compositions comprises providing crude monoglyceride compositions. Crude monoglyceride compositions typically contain at least 30% monoglyceride and at least 25% diglyceride, based on total weight of monoglycerides, diglycerides, and triglycerides therein. Typically they contain no more than about 70% monoglycerides, by weight, based on total weight of monoglycerides, diglycerides and triglycerides, and they are typically purified to provide a purified monoester composition having a monoglyceride presence of no less than 85%, based on total weight of monoglycerides, diglycerides and triglycerides in the purified monoester composition. Indeed, typically the purification processes will be practiced to achieve at least 90% monoglycerides, on such a basis, and in some preferred applications they will be practiced to provide at least 95% by weight monoglycerides in the purified monoglyceride composition.

When the practice is with monoesters other than monoglycerides, for example PGME's, similar results can be obtained. However, typically with PGME's the compositions will also include some propylene glycol diesters, as well as monoglycerides, diglycerides and triglycerides from processing. In such instances, the purification will generally involve selectively retaining monoglyceride with the purified PGME, relative to diglyceride and triglyceride. However an alternative is provided hereinbelow, in connection with FIG. 5.

Preferably the step of extracting with alcohol/water extractant comprises conducting a multi-stage counter-current extraction; typically with at least two stages and preferably at least three. Preferably the extraction is conducted at a temperature of at least about 60–80° C. and not greater than 120° C., so that triglycerides present will be in the liquid phase and the alcohol/water solvent will generate only relatively low pressures. Typically, the extraction with ethanol/water is conducted at about atmospheric pressure, and preferably at pressures no higher than 5 atmospheres.

Preferred processes include a step of back extracting or washing the alcohol/water extractant phase from the primary or first extraction. The step of back extracting or washing is preferably conducted with a triglyceride-containing phase, for further "tuning" of the purification, to reduce a presence of diglycerides that may have been extracted into the alcohol/water extractant, during the primary extraction. The step of back extracting or washing, then, can be referred to as a "wash" of the extractant from the primary extraction with a triglyceride-containing phase.

In some applications, the triglyceride-containing phase, from the step of washing, is added to the crude monoglyceride mixture, as a source of added triglycerides for conduct of the primary extraction. Preferably the step of washing also comprises a multi-stage counter-current washing; again typically having at least two stages, preferably at least three.

According to some aspects and applications of the present invention food additives are provided. In general, the food additives comprise purified monoglyceride (or other ester) component isolated or purified according to the present invention. In certain preferred systems involving purified monoglycerides, the purified monoglyceride (monoester) component comprises at least 85% by weight monoglycerides (or monoester), based on the total weight of monoglycerides (monoesters), diglycerides (diesters) and triglycerides (triesters) in the monoglyceride (monoester) component.

In general, typically when crude monoglyceride compositions are utilized, prior to addition of the triglycerides thereto, the crude monoglyceride composition comprises, by weight, no more than 20% triglycerides, based on total weight of monoglycerides, diglycerides, and triglycerides in the crude monoester composition. Again, preferably it contains no more than about 70% monoglycerides, by weight, based on total weight of monoglycerides, diglycerides, and triglycerides in the crude monoglyceride composition. In general, when monoglyceride purification is intended, the method can be characterized as being conducted to achieve the isolation of purified monoester composition, having: a monoglyceride presence of no less than 85%, based on total weight of monoglycerides, diglycerides and triglycerides in the purified monoester composition; and, a diglyceride-to-triglyceride weight ratio, in the purified monoester composition, of no greater than 1:1.

The present invention also concerns provision of a processing facility for purifying crude compositions. The processing facility generally includes a primary counter-current extractor as described; a secondary counter-current extractor as described; fluid direction conduit arrangements for preferred cycling and direction of materials; and, a source of triglyceride and a source of crude composition (for example, crude monoester composition to be purified) constructed and arranged as necessary, for provision of preferred operations. In some instances, additional extractors may be used.

DETAILED DESCRIPTION

Figure 1:
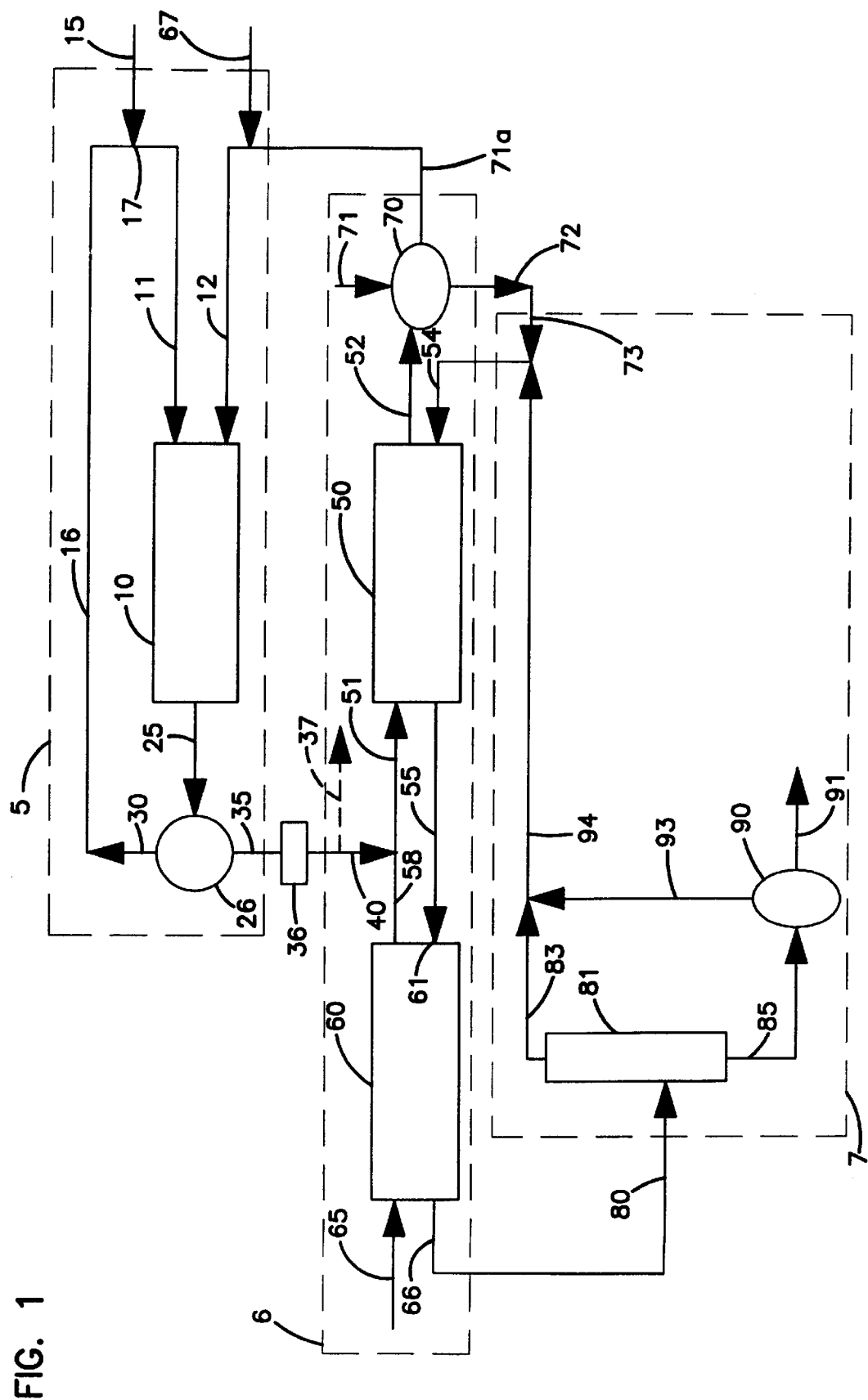
FIG. 1 is a schematic presentation of a process and equipment for practice of the process, according to a first described embodiment of the present invention.

The present invention concerns methods, techniques and equipment for purifying or isolating materials such as monoglycerides, diglycerides, and propylene glycol monoesters (i.e., target esters), from crude ester mixtures containing related diesters and related triesters (i.e., contaminating esters). The techniques described generally utilize preferred liquid-liquid extractions, to facilitate the process. Most preferred practices are conducted under conditions in which the monoester to be isolated (or any other isolated target ester) is not distilled at any point in the process. Preferably it is conducted without subjecting the crude ester composition, after formation, to temperatures in excess of 140° C. and/or pressures in excess of about 5 atm. Typically the processes described herein can be practiced without subjecting the crude ester composition, after formation, to temperatures in excess of 120° C. and/or pressures in excess of 3 atm. Also, typically, (at least in most preferred applications) no large amounts of materials such as non-alcohol solvents (propane, butane, hexane, ethers, ketones etc.) are used, during the step of extracting from the crude mixtures. Preferably none of these materials is used. Herein the term "no large amounts" in this context is meant to refer to no more than about 15–20%, by weight, of the referenced solvents.

I. Materials Purified

Glycerol is a 1,2,3-trihydroxy propane, or propylene triol. It is typically obtained from hydrolysis or alcohol reaction, of naturally occurring triglycerides, during fatty acid production. Propylene glycol is a 1,2-dihydroxy propane (1,2-propane diol). Propylene glycol is typically obtained from hydrolysis of propylene oxide. Techniques according to the present invention were developed to facilitate isolation and purification of target esters such as monoesters and/or diesters of such materials, from crude mixtures containing the monoesters and diesters (and in some instances triesters). The particular monoesters of greatest interest, are fatty acid monoesters, for example propylene glycol or glycerol monoesters of fatty acids. Herein the terms "isolation and purification" when utilized in this context, and in similar contexts, are not meant by themselves to specifically refer to some particular level of purity of the isolated target ester material, for example, monoester, other than an improved purity relative to the crude mixture. However, in typical applications, the technique can be utilized to obtain monoester purities of at least 85% (by weight), and usually preferably to obtain purities of at least 90%, relative to contaminating diesters and triesters (i.e., contaminating esters). In some specific applications, monoester purities of 95% or greater can be obtained.

It is foreseen that techniques according to the present invention can, for example, be utilized to isolate and purify a variety of monoesters, from crude mixtures of the monoesters with related di- (and/or tri-) esters. For example, according to the present invention, monoesters isolatable using the techniques typically comprise esters of $C_3$- or $C_4$-diols or triols, wherein each hydroxy group is on a separate, isolated carbon in the 3 or 4 carbon group. Typically, the applications will cover esters wherein the ester group is a straight chain $C_3$-multi-hydroxy compound. Typically the compounds will be monoesters of dihydroxy- or trihydroxy-substituted propane or butane.

Herein the term "fatty acid" is meant to refer to acids having at least 4 carbon atoms, typically, but not necessarily, 12 to 20 carbon atoms, and includes saturated and unsaturated fatty acids.

The fatty acids of greatest interest to the present invention are those derived from naturally occurring mixtures of oils or fats (or fatty acid derivatives) found in such fats and oils as: palm oil; soybean oil; canola oil; peanut oil; cottonseed oil; coconut oil; and, beef tallow. (The term "naturally occurring" in this context is meant to include reference to products from processing man-made hybrids or genetically altered plants or animals, as well as natural ones.) Such materials generally include mixtures of saturated and unsaturated fatty acid derivatives (fats) and primarily include fatty acid derivatives having an even number of carbons in the fatty acid backbone. They typically include predominately $C_{10}$ or greater acids, typically $C_{12}$ or greater. Herein when the term "$C_{10}$" is used in this context, it is meant that the carbon chain of the acid fragment, including the acid carbon, has 10 carbon atoms in it.

Reaction mixtures to be purified according to the present techniques can be made in a variety of manners. Typically they will comprise mixtures of mono-esters and di-esters, and in some instances trimesters, of a short chain di-hydroxy or tri-hydroxy compound. A desired result of the purification, when monoester isolation is intended, typically includes generation of a mixture comprising at least 85%, and typically at least 90%, by weight, monoester (relative to contaminating diester and, if present, triester), and more preferably at least 95% by weight, from a mixture comprising at least 30% and typically no more than about 70–80% (and sometimes no more than 60%) by weight of the monoester, typically about 35–65% by weight, based on total weight of monoester plus diester (and, if present, triester).

Although crude mixtures of monoesters to be purified according to the present invention may be obtained in a variety of manners, typically they comprise the reaction product of 3- or 4-carbon chain di- or tri-hydroxy compound, with naturally occurring fatty acid ester mixtures, typically triglycerides. Most typically, the crude mixtures will comprise the reaction product of either glycerol or propylene glycol with a naturally occurring triglyceride mixture such as palm oil, soybean oil, canola oil or sunflower oil. In some instances modified oils (such as partially hydrogenated oils or esterified oils) may be used.

Typical crude glyceride mixtures used in processes according to the present invention, especially for monoglyceride purification and prior to any triglyceride phase addition, will include monoesters and diesters in a weight ratio of about 0.75:1 to about 2:1 (mono:di), and in some instances may include a minor percentage (for example, up to 10–15% by weight) of triester, before any triglyceride addition to facilitate extraction. Typical crude monoglyceride mixtures, which will be purified using techniques according to the present invention, prior to any triglyceride-phase addition, comprise products having mono:di:triesters present in weight ratios of about 45:45:10 or about 60:35:5. These are the common crude monoglyceride mixtures, made in industry.

It is foreseen that crude monoglyceride mixtures containing variations from these amounts will be purifiable with techniques according to the present invention. However, the techniques were developed in a manner calculated to especially facilitate purification of such mixtures, because they are the types of mixtures prevalent in industry as crude monoglyceride mixtures.

When techniques according to the present invention are utilized for purification of monoesters such as propylene glycols, i.e., monoesters other than monoglycerides, generally analogous conditions and levels of purification to those described above with respect to monoglycerides are achievable. In such context, however, the weight percent of monoester stated will generally be based upon total weight of monoester, diester, and triester present, regardless, for example, of whether the diester and triester are glyceride esters or esters of the particular alcohol of concern, or a mixture of both. The latter will be typical, since, for example, propylene glycol monoesters are typically prepared from triglyceride and thus crude propylene glycol monoester mixtures will include propylene glycol diesters, monoglycerides, diglycerides and triglycerides.

II. Other Characterizations of Preferred Processing and Purity

A. Purity

In general, as explained above, techniques according to the present invention were generally developed to provide preferred overall levels of target ester purity, for example with respect to purified monoglycerides, in advantageous cost-effective manners. During the course of the study, however, it was discovered that while the absolute level of purity of the purified target ester (for example monoester) was of great importance, it was not the only factor of interest with respect to preferred products. In particular, it was found that in some instances, preferred products were obtained if there was a focus at least in part upon the content of the principal contaminating esters.

For example, as indicated above, when the material to be purified is a crude monoglyceride mixture, the mixture generally comprises monoglycerides, diglycerides, and triglycerides. During the studies, it was found that preferred purifications would occur if, with respect to the contaminating diglycerides and triglycerides, the purification was conducted in such a manner that the diglyceride to triglyceride ratio, by weight, was reduced to no more than 1:1 (and typically less), and typically and preferably to less than 1:3. Since crude monoglyceride mixtures generally contain greater percentage of diglycerides than triglycerides, by weight, by the above, it is generally meant that the process (for monoester purification) should be conducted in such a way that focus is on diglyceride removal/reduction.

In the same context, and as part of the same evaluations, it was observed that in general preferred purified monoglycerides not only contain at least 85% (and preferably at least 90%) by weight monoglycerides, but also have a monoglyceride-to-diglyceride ratio, by weight, of at least 40:1 and preferably at least 70:1. Again, typically and preferably, the majority of the contaminants in the purified monoglycerides, by weight, in such systems is preferably triglyceride (as opposed to diglyceride).

B. Processing

As will be apparent from the following discussions and examples, a variety of techniques have been developed for characterizing preferred steps of processing. Some of the more significant are as follows:

1. Loading: In general, processes according to the present invention will not be considered preferred or particularly effective unless the loading of the ester (for example, monoester) to be purified in the polar phase or extractant, is substantial. That is, with techniques according to the present invention, one is not only trying to obtain high selectivity during the extraction so that good purity results, but one is also seeking simultaneously a relatively high loading or at least substantial loading, so that the process is efficient. If loading is too low, the process will be commercially undesirable since high amounts of extractant would be needed. In typical preferred processes according to the present invention, including under the conditions described herein below, one can achieve loading of the monoester(s) in the extractant during the extracting process of at least 10 grams (g) per 100 g extractant, and typically loadings of at least 15 g per 100 g extractant (or more) are obtained. The term 10 g monoesters per 100 g extractant refers to the load in the extractant phase leaving the extraction step, for example at line 55, FIG. 1.

2. Selectivity: Processing according to the present invention can be characterized with respect to the selectivity of the extraction. When monoester purification is involved, this can be phrased in a variety of ways including the extraction selectivity for the monoester over the diester; the extraction selectivity for the triester over the diester; and, the selectivity of extraction for the monoester over the triester, when the process includes purification of mixtures including monoesters, diesters, and triesters. In monoester purification, a selectivity of particular concern will be the selectivity for the monoester over the diester.

In general, selectivity ($\alpha_{1,2}$ of component 1 to component 2) is defined by the ratio, for the extractant phase to the raffinate phase, of the ratio of concentrations, by weight, of component 1 to component 2. Thus, $\alpha$ is a ratio of ratios. From the examples given below, it will be understood that selectivities for monoester over diester of >5 and for monoester over triester of >50 can be readily obtained with processing according to the present invention.

III. Method of Purification—Generally

A. Monoglyceride Purification

In general, crude target ester mixtures, such as crude monoglyceride compositions, according to the pre sent invention are purified through liquid-liquid extractions. For example, monoglyceride values in the crude mixture are preferentially extracted into (partitioned into) an alcohol-containing phase. The separation/purification is facilitated by the following:

1. Provision of sufficient water in the alcohol-containing phase to provide desirable selectivity of extraction; for example, preferential extraction or partitioning of monoglycerides vs. diglycerides (or even triglycerides) into the alcohol phase; and 2. Provision in the non-alcohol phase of a component to facilitate solubility of diglycerides (and triglycerides) in that phase. Preferably this added component includes a triglyceride or a triglyceride mixture. Most preferably it is a naturally occurring food substance and does not contain substantial amounts (greater than 20% and preferably none) of non-functionalized organic solvent such as a hydrocarbon (propane, butane, etc.).

In general, purified monoglycerides, with monoester contents of greater than 90%, until now have been available commercially only as distilled monoglycerides. Because of the low vapor pressure, monoglycerides can be distilled only under relatively high vacuum and relatively high temperatures. This leads to a process which is rather expensive and which can lead to undesirable products. Unfortunately, distilled monoesters are also sometimes responsible for a bitter flavor in the finished product, limiting the level to which they can be added.

In many applications it is the monoester which is providing the desired functionality, with the attendant diester being present only as an unwanted byproduct. A source of more highly purified, low cost, monoesters can be, therefor, generally provided by the present invention.

In certain applications, the diester is in fact a detrimental component, and a higher price is paid in order to get the more highly purified, distilled monoester. In some instances, the presence of the diester is believed to modify the phase behavior of the monoester, interfering with functional activity.

It is true that some alternative purification processes have been contemplated in the art. Fractional crystallization, which utilizes differences in melting points between the monoesters and other components, is generally feasible only for products with narrowly defined fatty acid profiles, such as fully saturated oil of IV<2, where the fatty acids are dominated by a single species such as stearine. In this context the term "IV" refers to the iodine value, which is an indicator of the degree of saturation. Products with a range of IV will tend to fractionate by IV, rather than by degree of esterification.

Supercritical extraction using an extractant such as propane has been suggested as an approach to purification, but it is too expensive to be commercially viable. In general, it requires relatively high pressures (>60 atm) and involves relatively low loading (typically <5 wt % fat in the extractant wherein the term "fat" refers to whatever fatty acid ester is in the extractant.) It is noted that use of a non-polar extractant in supercritical extractant involves extraction of the di- and trimesters away from the monoester and into the extractant.

Adsorption techniques, wherein the monoesters are adsorbed onto a solid support and are later desorbed into a solvent, may be feasible but typically would require large amounts of resin, which can increase cost.

Until now, the use of liquid extractants in a viable system has not been developed or proposed. For example, low boiling hydrocarbons such as hexane could be envisioned to selectively extract the di- and trimesters, leaving the monoesters behind. In practice, however, the hydrocarbon has generally had too great a solvency and typically also extracted the monoglyceride, often forming a single phase system. A supercritical use of propane has been suggested as a method around these problems, but such an approach is impractical and is generally asserted to be prohibitively expensive. Alcohols or alcohol/water blends may also have been proposed to extract the monoesters, and leave the diesters and triesters behind. These approaches would not generally be commercially feasible, however, at least because in order to achieve the desired purity of the monoester, the solvent polarity would need to be adjusted to be quite high (large water content) so that the overall solubility of monoesters would be unreasonably low, resulting in excessive solvent requirements. A combined process, using a hydrocarbon and an alcohol/water extractant, would also be impractical on a large scale for many processes, because the hydrocarbon competes too strongly for the monoglyceride, resulting in low extraction factors and because recovering both the hydrocarbon and the alcohol/water adds cost.

The proposed preferred processes of the present invention, using an aqueous alcoholic extractant and using triglyceride fat/oil as a second phase to remove the diester, are unique and advantageous, but several obstacles needed to be overcome to obtain a useful process. For example, use of liquid-liquid extraction was perceived as counter-intuitive because the very nature of the desired product, monoesters, is that of an emulsifying agent. Such a product is used to stabilize emulsions of water in oil, such as triglycerides. The forming of a stable emulsion would prevent the operation of a liquid-liquid extraction system. The present process has worked satisfactorily in spite of this, although it is believed that low shear mixing will be useful and desirable in commercial scale practice, to prevent or inhibit formation of undesirable emulsions.

Secondly, triglyceride is one of the contaminating products in the crude monoglyceride stream, so intentionally adding triglyceride in order to help purify the-monoglyceride is counter-intuitive. However, adding triglyceride has proven to be very useful in reducing the level of diester present in the final product, when the desired final product is the monoester fraction.

Thirdly, residual triglyceride in the product is not readily removed (compared to a low boiling hydrocarbon such as hexane). However, it is believed that an important factor in defining purity of the monoester product may be how low the diester content is, or the ratio of monoester to diester content, rather than the absolute level of monoester content, or even the level of triester if it is below a threshold amount. After all, the purified monoester is frequently added to products along with triglycerides in the emulsified shortening. Thus, the purified monoester, in use, may well be mixed with triester, and it is generally removal of diester which is of greatest concern.

Indeed, in some applications, a product with a weight ratio of 90/5/5 monoglyceride, diglyceride, triglyceride may well be superior in functionality to one of 90/10/0. The greater difference in functionality between the monoester (monoglyceride) and the triester (triglyceride) is believed to cause triglyceride to be less interfering in the ability of monoester to form mesophases, than would be the same weight of diester.

It is also noted that the amount of triglyceride required, to facilitate the separation and purification, has been found to be relatively small. If, as an alternative to the triglyceride, a hydrocarbon, such as hexane, were to be used to facilitate the separation, a typical concentration might be 5–10 wt. -% of di- and triglyceride in the hexane. At this level, one might expect cosolvent effects, if any, to be relatively small and the system would behave as a hexane solution. Note that this corresponds to a system 0.7–1.5 mole % diglyceride in hexane, giving more than 65 molecules of hexane for every molecule of diglyceride. If triglycerides were needed at the same molar level as the hexane, the required amount of triglyceride would be at least 90 times, by weight, of the diglyceride stream or a concentration of less than 1.1 wt % diglyceride in the triglyceride stream. However, in preferred embodiments of the invention, where the triglyceride stream is subsequently used to generate more monoglycerides, the maximum level of triglycerides used (i.e., added) typically is only about 1.5–3 times by weight of the diglycerides, and in other preferred embodiments it is expected to be no more than 8 times by weight of the diglycerides. The preferred minimum level of added triglycerides is expected to be greater than about 1 time by weight the diglycerides. At these levels of concentration, significant cosolvent effects are expected, and the system would not be characterized as a triglyceride stream, but rather as a mixture of di- and triglyceride.

It also might be expected that the diglyceride would act as a strong solvent to the monoglyceride, resulting in the ineffective extraction of the monoglyceride by the alcohol/water stream and leading to poor yields. This, however, has not been found. Based on batch results, it is anticipated that the extraction yield (extraction of monoglycerides into the alcohol/water extractant) in a countercurrent extraction train will exceed 90 wt % of the monoglycerides present in the feed.

Typically and preferably the extraction process, for monoester purification, is conducted at about 60° C.–80° C., and not above 120° C. Also, typically and preferably it is conducted at about atmospheric pressure, and not above 5 atm. Also, typically and preferably the alcohol layer comprises 60–90% alcohol and 10–40% water, by weight. Most preferably it comprises about 70–85% alcohol, and 15–30% water, by weight. It is foreseen that typical preferred alcohol/water layers into which the monoglycerides are extracted will comprise about 75% alcohol/25% water, especially when the alcohol is ethanol. The typical and preferred alcohol will be ethanol because of high selectivity, high loading, low cost and acceptable toxic character.

Preferably the triglyceride added to the crude mixture comprises the same triglyceride as is present in the crude mixture prior to triglyceride addition. That is, in typical instances the crude monoglyceride mixture that is to be purified will have been made from a triglyceride mixture; and, the same type of triglyceride mixture which was used to make the crude monoglyceride mixture is the one added to the resulting crude monoglyceride mixture, prior to the extraction of the monoglyceride values into the alcohol/water feed, to facilitate the extraction. For example, if the process is used to purify a crude monoglyceride composition isolated from soybeans, then preferably the triglycerides added to the crude monoglyceride mixture to facilitate the extraction will be a crude mixture from soybeans, i.e., soybean oil, preferably with the same degree of hydrogenation. Advantages as a result of this will be apparent from the following more detailed descriptions.

B. A Process Flow Diagram

In FIG. 1, a preferred process flow for isolation and purification of monoesters such as monoglycerides according to the present invention is provided. The flow diagram of FIG. 1 is intended to be representative of more generally preferred applications according to the present invention. It is foreseen, however, that principles according the to present invention may be applied in variations from the process schematic shown in FIG. 1.

Referring to FIG. 1, the process generally includes three stages; i.e., Stage I (reference 5); Stage II, (reference 6); and, Stage III (reference 7). In Stage I, crude monoglyceride (monoester) mixtures are prepared. In Stage II, separation of a purified monoglyceride (monoester) mixture from a raffinate or residue mixture, is conducted. In Stage III, purified monoglycerides (monoesters) are isolated from the purified monoglyceride mixture. It is foreseen that Stages I, II and III can be conducted at one facility or more than one facility; and, they can be conducted in a batchwise or continuous process. However, it is noted that in one particularly preferred conduct of a process according to the present invention, cycling of certain feeds can be utilized to advantage. In such systems, generally the entire process will be conducted at a single facility. It may also be preferred in some applications to develop and use equipment that can be operated in a continuous flow-through process format, rather than a batch format, for efficiency.

1. Stage I—Generation of Crude Glyceride Mixture

As indicated above, the first stage of the process of FIG. 1, is indicated generally at reference 5, and comprises a stage whereat the crude glyceride mixture is generated. In general, the mixture is prepared in reactor 10. It is generated from a feed of glycerol 11 and a feed of triglyceride 12. In the reactor 10, the glycerol feed 11 and triglyceride feed 12 are mixed, and a mixture including monoglyceride(s) and other materials, typically diglyceride(s) and triglyceride(s), is generated. The reactor 10 is generally operated at about 220–260° C., and under atmospheric pressure, although a variety of conditions may be utilized. The reactor 10 may be operated in a batch manner, or as a continuous process. Typical conventional operations for crude monoglyceride production can be utilized, and would involve a batch operation, with some base added as a catalyst. The typical base utilized will be sodium hydroxide or sodium glycollate.

The glycerol feed 11 may comprise either: an added glycerol stream from outside sources; a glycerol recycle stream from the reactor 10, as described, or both. Typically glycerol feed 11 will include both: added glycerol, indicated at 15; and, a glycerol recycle stream 16, as described. Streams 15 and 16 can be combined, at 17, using various metering techniques to obtain a preferred composition of glycerol feed in stream 11, to the reactor 10.

The triglyceride feed stream 12 may comprise an outside source (for example, natural product source) of triglyceride, cycled raffinate from an extraction step in Stage II, or both. Diglycerides will be present in the cycled raffinate and are a preferred feed component in the triglyceride feed stream. Typically and preferably feed 12 will include both. It is noted that naturally occurring triglycerides, such as palm oil or sunflower seed oil, are typically mixtures of triglycerides. More specifically, they comprise a mixture of fats or oils including the triglycerides of numerous fatty acids.

Still referring to Stage I (reference 5), reference 25 generally indicates the exit stream from reactor 10. Generally the exit stream 25, which comprises glycerol and a glyceride mixture, is directed into separator 26.

Either in separator 26, or immediately upstream, the reactor offstream 25 is preferably cooled, for example to about 60–120° C., and typically the base catalyst is neutralized with an acid, usually phosphoric acid. Under these conditions, the glycerol will separate as a separate phase, since it is relatively insoluble in the glyceride mixture. At 30, the glycerol phase is shown removed from separator 26. In the particular system depicted, the glycerol phase from separator 26 is directed for recycling, i.e., into recycle stream 16. The crude monoglyceride-containing fraction is shown removed from the separator 26, through line 35. Thus, line 35, in combination with a remainder of Stage I, represents a source of crude monoglycerides. It is arranged for direction of crude monoglycerides into an inlet feed of a primary counter-current extractor, as described below.

In general, the crude monoglyceride (monoester) phase from separator 26 will include some residual glycerol (alcohol) therein. Preferably, before it is directed into Stage II, it is treated to reduce the residual glycerol (alcohol) presence to less than 1% by weight. This can be conducted by a stripping step to remove residual glycerol. Equipment for conducting this is shown at 36. In general, any effective stripping step/equipment may be used, although a thin film evaporator or wiped film evaporator operating under vacuum will typically be preferred. Such stripping equipment would, of course, be useful to remove other volatile components such as free fatty acids.

At 37, an optional crude monoglyceride bleed is shown. It is foreseen that since there will be some commercial demand for the crude monoglyceride mixture, in some systems it will be preferred to have a bleed 37 so it can be drawn off (or partially drawn off), and not be directed in Stage II, if desired.

At 40, the crude monoglyceride mixture to be purified is shown directed into Stage II (reference 6).

As explained above, a variety of methods can be used for generation of the crude monoesters (monoglycerides). For example, as an alternative to being prepared from the reaction of glycerol with triglycerides, a crude mixture of mono- and diglycerides can be prepared from the reaction of glycerol with either fatty acids or with esters of fatty acids, such as methyl- and ethyl-esters. The equilibrium reaction product will generally comprise a crude mixture primarily of monoglycerides and diglycerides, with smaller amounts of triglycerides. The follow-up liquid-liquid purification process will be suitable for these reaction products as well.

2. Stage II—Liquid-Liquid Extraction

In general, in Stage II, crude monoglyceride is treated, through a liquid-liquid extraction, for isolation of a purified monoglyceride stream. Referring to FIG. 1, Stage II is generally indicated at reference 6. At 40, the crude monoglyceride stream is shown directed into Stage II for processing. In general, for preferred processes according to the present invention, the crude monoglyceride stream 40 is generated from a Stage I process, as described.

Preferred processes according to the present invention are conducted in such a manner that after the crude monoester composition is directed into Stage II, from then until isolation of the purified target ester (for example, monoester): the monoester (or other target ester) of interest is not distilled; the monoester (or other target ester of interest) is not subjected to temperatures in excess of about 140° C.; and, processes conducted under pressures greater than about 5 atm are avoided. Also in some preferred applications, no materials other than water, alcohol, triglyceride mixtures and similar generally recognized as safe materials, are added or used from that point forward in the process. Preferably hydrocarbon solvents (propane, butane, hexanes, etc.) are avoided to advantage, or if used are used in relatively small amounts.

In Stage II, reference 50 generally indicates the primary extraction equipment. Typically and preferably the extraction will be conducted at 60°–80° C., to ensure that it is conducted at a temperature above the melting point of any triglyceride component without being undesirably high. In general, the feed of monoglyceride mixture into the primary extractor 50 is shown at feed line 51; and, at line 52, the raffinate, i.e., the mixture substantially depleted with respect to monoglyceride values, is shown removed from the extractor 50. Herein when it is said that the mixture is "substantially depleted" with respect to "monoglyceride values" (or monoester values) it is meant that the monoglyceride (monoester) presence in the mixture has been reduced by at least 20%, due to extraction into a different phase, and separation. Typically and preferably at least 85%, and indeed at least 90% by weight of the monoester is extracted into the extractant.

At 54, the feed line for the phase into which the monoglyceride is extracted (i.e., the extractant) is shown directed into extractor 50. At 55, extractant, containing extracted monoglyceride values, is shown leaving the primary extractor 50. The material in line 55, then, comprises the liquid phase having the extracted monoglyceride values therein, i.e., it is a purified monoglyceride according to the present invention. This material is directed to Stage III, in typical processes, for separation of the monoglycerides (monoesters) from the extractant.

Still referring to FIG. 1, in Stage II (reference 6), the material in feed 51 to the primary extractor 50 generally and preferably comprises: crude monoglyceride from line 40; and, triglyceride feed from line 58. That is, prior to being directed into primary extractor 50, crude monoglyceride compositions are modified by the addition of triglycerides thereto, and line 58 represents the source of added triglycerides. This will facilitate separation in the primary extractor 50, since the diglyceride components of the crude monoglyceride mixture will even more preferentially remain in the triglyceride-containing raffinate, rather than partition into the monoglyceride-containing alcohol/water phase. In typical processes, the alcohol/water feed will comprise, by weight, about 1 times to 6 times the weight of the monoglyceride-containing stream fed into the extraction.

For the preferred system shown in FIG. 1, Stage II includes a secondary extractor 60 (or wash system). The secondary extractor 60 is used to advantage in the following manner. The offstream 55 from the primary extractor 50 is directed into the secondary extractor 60, as indicated at inlet 61. Within the extractor 60, relatively less polar components such as diglyceride component in the purified monoglyceride stream 55 are preferentially washed into the triglyceride feed or triglyceride phase, from the alcohol/water purified monoglyceride phase (i.e., back extracted or washed). This triglyceride phase is shown directed into the secondary extractor 60 at line 65. Thus, within secondary extractor 60, the monoglyceride-containing alcohol/water phase from primary extractor 50 is extracted (or back extracted) with a triglyceride-containing phase, generating a triglyceride phase exiting extractor 60 in line 58, and an even further purified monoglyceride containing alcohol/water phase exiting secondary extractor 60 at 66.

In the system of FIG. 1, the triglyceride exiting the secondary extractor 60 is fed into the primary extractor 50, and to a certain extent is even cycled into reactor 10. Referring again to Stage I, if still further triglyceride needs to be fed into the feed stream 12 to reactor 10, it can be added via line 67.

In the preferred arrangement shown, the crude monoglycerides are added to Stage II downstream from the secondary extractor 60 and upstream from the primary extractor 50.

Still referring to FIG. 1, Stage II (reference 6), the exit flow 52 from primary extractor 50 is shown directed into separator 70. Water is added to separator 70, at line 71. Thus, at separator 70 an aqueous phase and an organic phase will be generated. The organic phase is shown removed from separator 70 at line 71a, for direction into the triglyceride feed 12 to reactor 10. The aqueous phase is shown leaving separator 70 at line 72, for addition into the phase used in primary extractor 50, via line 73. This separator (which may contain more than one stage) is used to reduce the alcohol content in stream 52. Additional reduction in alcohol and water in stream 71a may be achieved by vaporization under vacuum.

Still referring to FIG. 1, Stage II, as indicated above, the monoglyceride enriched alcohol/water phase is shown leaving the secondary extractor 60 at line 66, for direction into Stage III.

Herein the term "fluid direction conduit arrangement" is used generally to refer to the various fluid conduits in the system for directing fluid flow between the various reactors, separators and extraction equipment. For example, the fluid direction conduit arrangement includes a fluid conduit 58 from the triglyceride extractant outlet of the secondary counter-current extractor 60, to the crude monoester composition inlet feed 51 of the primary counter-current extractor 50; and, it also includes a fluid conduit 55 from the alcohol/water extractant outlet of the primary counter-current extractor 50, into the secondary counter-current extractor inlet 61. These portions of the fluid direction conduit arrangement are generally found in Stage II, FIG. 1. The term "fluid direction conduit arrangement" is intended to include within its scope any pipes, fittings, pumps, valves, or other equipment needed or desired for appropriate operation.

3. Stage III—Monoglyceride Isolation From The Alcohol/Water Mixture

At this point, the purified monoesters are present as a solution in aqueous alcohol. A number of options are available to recover the monoesters into a useful form (i.e., as a target ester-containing food composition). For example, the aqueous alcohol/purified monoester stream could be back extracted with a low boiling hydrocarbon, such as hexane, and the hexane could then be stripped from the monoglycerides. The recommended hexane volume for such an operation would typically be a mass flow rate at least equal to the aqueous alcohol flow rate, in order to recover a significant portion of the monoglycerides.

An alternative method for recovery would be to cool the aqueous alcohol/monoglyceride stream to precipitate or crystallize the monoglycerides. In general, the "best" temperature for the cooled stream would be a function of the degree of hydrogenation of the monoglycerides. Satisfactory results would typically be obtained at temperatures of about 10–30° C.

A third method for product (target ester-containing food composition) recovery would be to add water to the aqueous alcohol/monoglyceride stream, reducing the solubility of the monoglycerides. Adding sufficient water to make an aqueous alcohol of greater than 50 vol. % water, and preferably greater than 70 vol. % water has been observed to cause separation of a significant portion of the monoglycerides. In general, centrifugation has been found useful for separating the two phases after the water addition.

A still further method of product recovery is to flash or distill the alcohol (ethanol), preferentially to the water, from the solution in order to form a more water-rich aqueous alcohol solution, resulting in easier separation of a monoglyceride-rich phase.

Another method to recover the product is to strip, preferably under vacuum, the water and alcohol (ethanol) to form a molten stream of substantially pure, dry, monoglycerides. A thin film, wiped film, or scraped film evaporator would typically be preferred choice for the final stripping, while a shell and tube evaporator might be useful to remove the bulk of the aqueous alcohol.

A still further method to recover product would be to spray dry under vacuum, preferably with a solid carrier such as flour or milk solids to aid in producing a granular product. Freeze drying can also be a useful technique to remove the final traces of aqueous alcohol from a concentrated stream.

Bearing these various possibilities in mind, general reference will be made to FIG. 1, and the isolation. From the above discussions, variations in equipment to accommodate different approaches to isolation will be apparent.

Reference 7, FIG. 1, generally represents Stage III, i.e., the stage whereat the monoglyceride enriched (or monoester enriched) alcohol/water liquid phase is treated for isolation of monoglyceride (monoester) values therefrom, as a target ester-containing food composition. In general, this phase is shown leaving the liquid-liquid extraction process, Stage II line 66, and is shown directed into Stage III, at 80. For the particular preferred system shown, in Stage III, feed 80 is directed into a distillation apparatus 81. The distillation apparatus 81 is operated to distill or vaporize the alcohol/water mixture, shown exiting at line 83, from the reactor bottoms containing purified monoglycerides, shown leaving the distillation apparatus 81 at line 85. The distillation apparatus 81 is preferably comprised of multiple stages. In the first stage, the bulk of alcohol/water mixture is preferably removed in an evaporator capable of handling a large volatile content, such as a rising film evaporator, falling film evaporator, shell and tube evaporator, or other equipment. The temperature should be maintained at 140° C. or less, preferably less than 100° C. at suitable pressure/vacuum for the alcohol/water mixture being used. Multiple effect evaporators might be used to achieve greater energy economy. In the later stage, the remainder of the alcohol/water mixture is removed to create a devolatilized molten product. A thin film evaporator or wiped film evaporator is believed to be suitable for this stage. This can be conducted with temperatures of about 140° C., and preferably no higher than 100° C., and at pressures of 200 mm Hg or less, preferably 50 mm Hg or less. Thus, within distillation apparatus 81, the monoglycerides are preferably not themselves distilled, but rather the ethanol/water solvent is distilled (or stripped) from the monoglyceride reactor bottoms. It is important to understand that in most preferred operations of systems according to the present invention, the isolated monoglycerides are not themselves ever actually distilled.

Still referring to Stage III, FIG. 1, the ethanol/water distilled away from the mixture, at line 83, is shown being cycled into the primary extractor 50, Stage II. The distillation bottoms 85, containing monoglycerides, are directed into separator 90. In separator 90, they can be washed with water or ethanol, for further purification, and recrystallization can be conducted, if desired. Purified monoglycerides from separator 90 are removed through line 91. If desired, alcohol/water or water utilized for separation or purification in separator 90 is shown directed via line 93, into line 94, whereat it is mixed with the distilled ethanol/water from line 83, and is cycled into the primary extractor 50 via line 54. In a preferred embodiment, the distillation bottoms 85 are of the desired purity and devolatilized to an extent that the separator 90 can be bypassed, and the distillation bottoms 85 can be further processed, as described below for the product via line 91.

The purified monoglycerides (food composition) shown removed from separator 90 via line 91 can be sold as product, or further processed, for example by drying, flaking, pelletry, hydration or mixing with triglyceride fat/oil.

From the above discussion of FIG. 1, it is apparent that processes according to the present invention are particularly advantageous, since they are well developed for efficient operation to facilitate generation and isolation of monoglycerides. For example, the triglycerides added to facilitate the separation, in Stage II, are cycled into Stage I, to facilitate preparation of the monoglyceride mixture. Preferably, ethanol/water utilized as the liquid phase into which the partitioning of monoglyceride occurs during the liquid-liquid extractions, is cycled back into Stage II, following isolation of the monoglycerides therefrom, to advantage.

Utilization of primary and secondary extractors 50 and 60 respectively, in Stage II, is unique and highly advantageous. The extraction which occurs in secondary extractor 60 is of diglycerides into a triglyceride-enriched feed, and results in a fine tuning of the purified monoglyceride stream 55, for preferred partitioning of diglycerides that may be present into the triglyceride feed. Thus, any diglyceride presence, from extraction into the water/ethanol phase in extractor 50, is greatly reduced.

Line 51, directed in the primary extractor 50 includes triglyceride-enriched crude monoglyceride mixture. The term "triglyceride-enriched crude monoglyceride mixture" as used herein, in this context, is meant to refer to a crude monoglyceride mixture to which triglycerides have been added. (Of course, the triglyceride-enriched crude monoglyceride mixture is itself a crude ester composition.) Preferably the triglyceride-enriched crude monoglyceride mixture is a mixture to which there has not been an addition of other non-alcoholic solvents, beside the triglycerides, i.e., hydrocarbon solvents such as propane, butane, hexanes, etc. That is, preferably the monoglyceride mixture is modified by addition thereto of triglycerides, but not by addition of other solvents, to facilitate extraction.

The triglyceride(s) generates a preferred organic phase for partitioning and separation, in the primary extractor 50. In particular, it creates an environment in greater contrast to the alcohol/water environment of the extractant, so that the diglyceride component will more preferably remain in the organic phase, relative to partitioning into the alcohol/water phase. Diglyceride which does partition into the alcohol/water phase, however, can be greatly removed in the secondary extraction process. In general, then, in processes according to the present invention the composition of the phases in the primary extractor 50 and secondary extractor 60 will be balanced to achieve a preferred efficiency of separation.

An improved system to that shown in FIG. 1 has been devised. In general, it has been observed that some of the colors and flavors from crude monoglycerides concentrate in the extractant phase, during the Stage II extractions, and remain in the final product from Stage III. This is reasonable, given that the extractions generally will remove the monoglycerides and anything else present which is more polar than the monoglycerides. An approach has been developed to control this, which is to treat the crude monoglyceride stream with a prewash, using a relatively dilute polar solvent such as alcohol, in order to wash out some of the impurities. Appropriate control of the alcohol content can be used to minimize monoglyceride loss. Such a prewash would remove (or reduce the level of) undesirable components such as free fatty acids, some glycerin, catalyst residues and catalyst neutralization residues. Example 14, described hereinbelow, shows the solubility of monoglycerides as a function of water content in the polar phase. With this type of information, one can develop a suitably polar wash for the crude monoglyceride mixture that will result in some removal of the polar contaminants, without undesirable levels of removal of monoglycerides.

Figure 2:
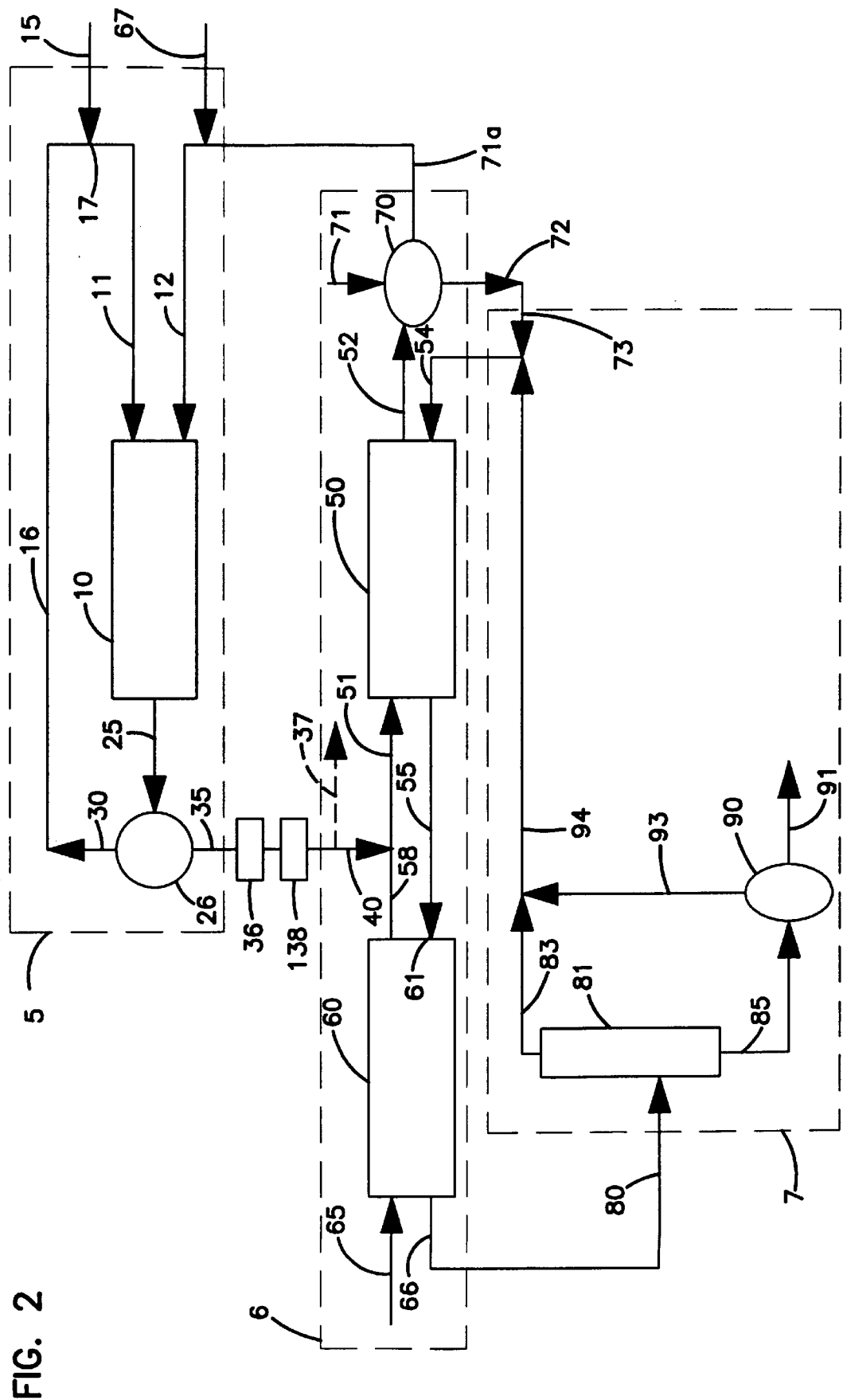
FIG. 2 is a schematic presentation of a process and equipment for practice of an alternate embodiment, to that described in connection with FIG. 1.

A flow chart depicting a system with such a wash therein is depicted in FIG. 2. FIG. 2 is identical to FIG. 1, but for the presence of the apparatus for the washing step shown at 138. After the wash, the crude monoglycerides, washed for removal of some polar contaminants therein, would be directed via line 40 into Stage II, as shown and described above.

It is noted that in some instances, the stripper 36 may be replaced with the equipment 138 for conducting the washing step. It is foreseen that a typical wash stream would be a countercurrent wash comprising a water/ethanol mix of about 44% water, 56% ethanol (by wt.).

IV. Preferred Conduct of the Extractions

In general, when processes according to the present invention are practiced with both a primary extraction and a follow up wash step (i.e., the secondary extraction), the process may be characterized as a liquid-liquid fractionation or fractional extraction. With such practices, the ultimate purity obtained for the monoesters approaches 100%, generally limited only by the solubility of the wash solvent (i.e., the triglycerides) in the extraction phase.

When processes according to the present invention are conducted without the secondary extraction, or wash step, the ultimate purity obtainable for the isolated monoesters is essentially limited by the ratio of monoesters and diesters in the crude, and the selectivity, $\alpha$, of the solvent. Selectivity (for monoester versus diester) is generally given by the formula:

$$\alpha = K_{mono}/K_{di}$$

wherein the K's are partition coefficients (extraction coefficients) defined as K=y/x, where y is the mass fraction of the relevant material in the extract, and x is the mass fraction of the relevant material in the raffinate phase. Of course similar formulae can be written for selectivity of monoesters versus triester, or diester versus triester.

For extractions involving a large number of stages, the monoester purity (excluding triglyceride) is given by the formula:

$$\%\,ME = 100 \times \left[\frac{r \times \alpha}{1 + (r \times \alpha)}\right]$$

wherein r=ME/DE (mass ratio) in the crude (ME being monoester, DE being diester). Under some typical conditions, involving monoglyceride isolation, a composition of the crude would typically be about 60 wt % monoglyceride, 35 wt % diglyceride, and 5 wt % triglyceride, giving an r equal to 1.71. The required value of $\alpha$ to achieve a desired monoglyceride purity can then be calculated, with $\alpha$=5.3 for 90% MG and $\alpha$=11.1 for 95% MG purity. Requiring a greater than or equal to 11.1 limits the aqueous alcohol compositions and levels of monoglycerides which may be used. This is in sharp contrast to the system with a wash section, or secondary extraction, where there are no similar restrictions on $\alpha$, since the secondary extraction or wash removes or reduces undesired diglycerides from the extractant.

Thus, in general, a preferred level of purification of monoglycerides in preferred systems according to FIG. 1 is generally obtained through control of:

1. The conditions of the primary extraction;
2. The conditions of the secondary extraction; and
3. The relative conditions of the primary extraction and second extraction.

In general, fatty acid esters such as monoglycerides and diglycerides are insoluble in water but are very soluble in low molecular weight alcohols, i.e., $C_1$–$C_3$ alcohols such as ethanol. However, although diglycerides are somewhat soluble in aqueous ethanol, they are less so than monoglycerides. The liquid phase into which the monoglyceride is extracted in the primary extractor 50, then, is preferably a phase comprising a mixture of alcohol and water. The mixture should be tuned to obtain a preferred amount of monoglyceride partitioning therein, with control on a preferred maximum amount of diglyceride partitioning which also occurs in that stream. The amount of diglyceride extraction into that stream, which can be accepted, turns in part upon the level of diglyceride removal which can be readily conducted in the secondary extraction. The more water which is added to the ethanol, the more specific will be the partitioning between diglyceride and monoglyceride in the primary extraction. That is, with an increase in water, the liquid phase into which the monoglyceride is being extracted has a lower propensity to also pick up (extract) diglycerides, i.e., the extraction is more selective. Of course it also has a lower propensity to pick up monoglycerides.

In general, it is desired to utilize conditions in which relatively high load of monoester (extracted ester) can be obtained. By this it is meant a load of at least about 10 g (preferably at least 15 g) per 100 g extractant. Thus, it is undesirable to add so much water that that solubility of the monoester (extracted ester), under the extraction conditions, is below these preferred amounts. This will involve some sacrifice in purity, at least at the primary extraction stage. However, the secondary extraction or washing in preferred applications, addresses this.

Similarly, the amount of triglycerides added (to the crude ester or crude monoglycerides) to facilitate a separation, will depend upon the level of partitioning with respect to the diglycerides preferred. The more triglycerides added, the lower will be the propensity of the diglycerides to partition into the alcohol and the greater will be the propensity of the diglycerides to remain in the organic (triglyceride/diglyceride) phase during the primary extraction. Thus, the level of triglycerides added can be balanced with the ethanol/water mix, to obtain a preferred partitioning of diglycerides.

A variety of extraction techniques, and extraction equipment, can be utilized for both the primary extractor 50 and secondary extractor 60. In general, counter-current extractors will be preferred, typically configured for at least two stages and more preferably at least three stages in each extraction. The choice of the number of stages is based on the desired extend of recovery, purity and overall economics. For a given recovery and purity, a system with more stages will allow higher loading of the extractant phase, reducing product recovery costs. In a typical and preferred system, the loading will be at least 10% by weight, monoester in the extractant. In more preferred systems, the loading will be at least 15% by weight, monoester in the extractant.

Typically, the amount of triglyceride fed into the system will be balanced with the amount of purified monoglyceride and crude monoglycerides removed so that the system operates at steady state with neither accumulation nor depletion. While maintaining the constraints of material balance, triglyceride can be fed into the system through either line 67 or line 65. In preferred embodiments, the triglyceride is fed primarily through line 65. This maximizes the triglyceride flow through the extractor, diluting the diglyceride, while allowing high purity monoglyceride production with a smaller extractant flow rate. This results in higher loading and reduced product recovery costs. If the flow rate through line 37 is more than about 4 times the flow rate through line 66 additional triglyceride may be needed, and it can be fed through line 67, to obtain higher extractant loading.

V. Propylene Glycol Monoester (PGME) and Other Monoesters

Processes as shown in FIG. 1, generally described above, can also be utilized to isolate other monoesters, for example propylene glycol monoesters, using analogous techniques. In general, the feed in line 11 would include propylene glycol, from line 15. Thus, the recycle at 30 in 16 would be propylene glycol, and the crude mixture at line 35 would comprise a mixture of propylene glycol monoester with diester and mono-, di-, and triglycerides.

In general, the preparation of propylene glycol fatty acid esters is possible from a number of routes. For example, propylene glycol and triglycerides can be reacted together to give a reaction product comprising primarily monoesters of propylene glycol, with lesser amounts of propylene glycol diesters, monoglycerides, diglycerides, and triglycerides, after removal of the excess propylene glycol and glycerol. A second route is through the reaction of propylene glycol with fatty acid or fatty acid esters, such as methyl or ethyl esters of fatty acids. The product from this reaction will generally be a mixture comprising primarily mono and di-esters of propylene glycol. A third route is to react propylene oxide with fatty acid, leading to a mixture of monoester isomers.

The proposed liquid-liquid purification process described herein will be useful for materials prepared at least according to the first or second routes. It is presently believed that the products from the first reaction scheme would be readily separated in a stream comprising primarily propylene glycol monoester and monoglyceride, and, if desired, the process could be tuned to provide a stream comprising primarily propylene glycol monoester. The reaction product from the second scheme is believed to be readily separable into a substantially pure propylene glycol monoester stream.

As to the third approach, the monoesters are generated in a substantially pure form.

The following may be useful, for considering a system for purifying PGME. Typical crude PGME product, made from reacting propylene glycol with triglycerides, would include, by weight, about 60–65% PGME; about 5–10% propylene glycol diester; about 10–15% monoglyceride; about 5–9% diglyceride; and about 5–8% triglyceride. The purification approach described herein would generally lead to an isolation of much of the PGME and MG values, from the remainder. It would particularly concern reductions in the diester and diglyceride amounts. The triglyceride amount may still be relatively significant, in the final isolated material. However, the material will still be preferred, due to the reduction in the presence of diglycerides.

If operated according to FIG. 1, the resulting composition would consist primarily of monoglycerides and PGME, with some diglyceride. The propylene glycol diester and the triglycerides present in the crude mixture would be largely removed. The extractant would likely contain less water than in the analogous monoglyceride purification, in order to increase solubility of the PGME in the extractant phase. If the crude PGME product had an initial composition as reported above, it is anticipated the final product would have a composition of roughly 75–80% PGME, 15% monoglyceride, 3–6% diglyceride, less than 1% propylene glycol diester and 2% triglyceride. To get significantly higher purity would require removal of monoglyceride. This component is more polar than the PGME and may be removed using a separation as shown in FIG. 5.

Figure 5:
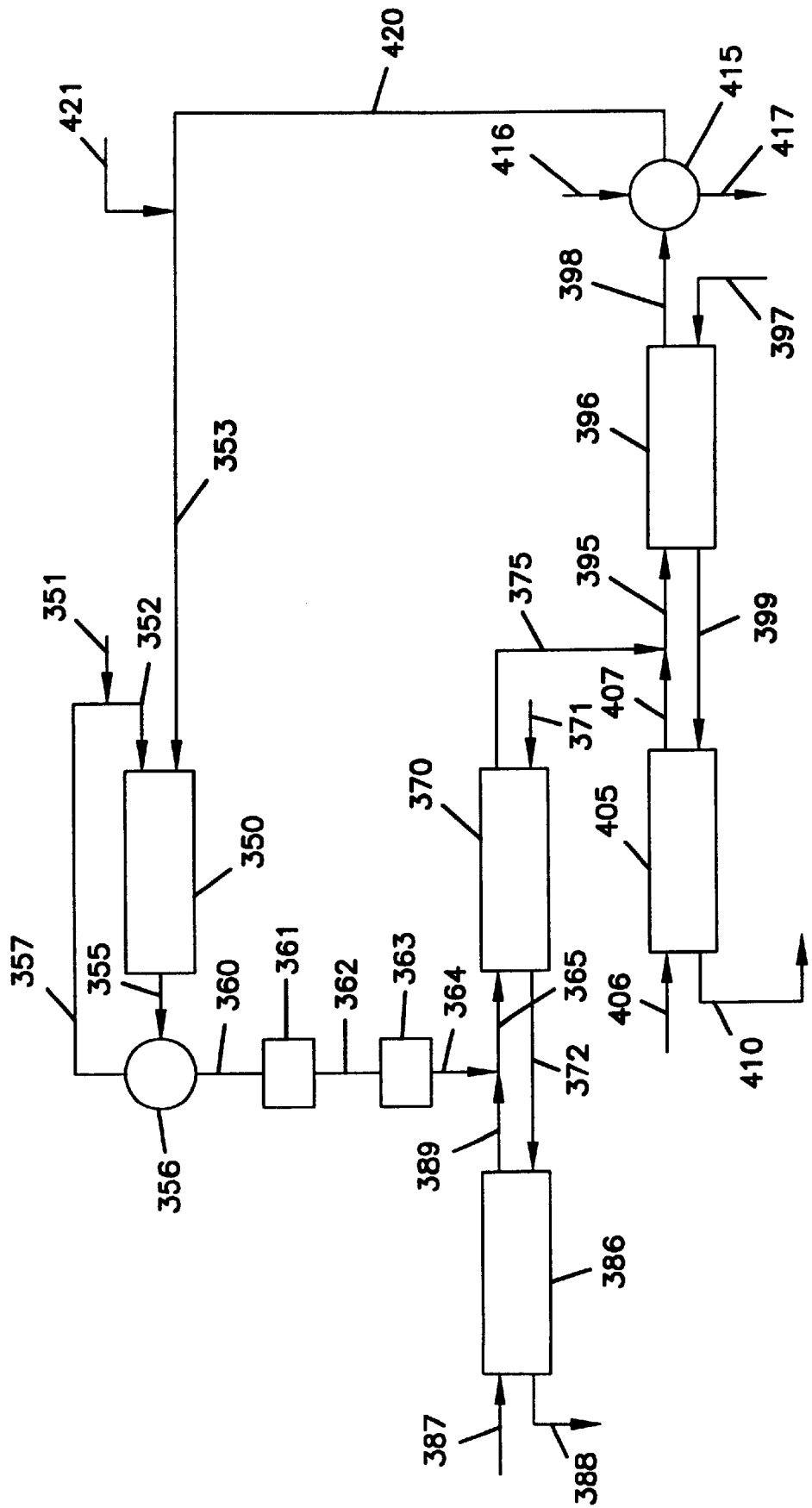
FIG. 5 is a schematic presentation of a process and equipment for practice of the process, according to a preferred application for isolation of a purified propylene glycol monoester stream.

In FIG. 5, a schematic depiction of equipment and processing steps for isolation of propylene glycol monoesters from a mixture is shown. Referring to FIG. 5, reactor 350 is a reactor in which propylene glycol is reacted with triglyceride, to provide a mixture of propylene glycol esters. Propylene glycol feed into reactor 350 is shown via lines 351 and 352. Via line 353, a triglyceride feed into reactor 350 is shown.

The conditions of reactor 350 will be such that the propylene glycol will be esterified by fatty acid chains of the glyceride mixture. Thus, leaving reactor 350 via line 355 will be a mixture of propylene glycol esters and glyceride esters. It is foreseen that typical conditions within reactor 350 will be 180–250° C., about one atmosphere of pressure or less (and generally not greater than a few atmospheres). Also, there will typically be a catalyst content in the reactor 350, for example, typical transesterification catalysts such as sodium hydroxide or sodium glycollate, etc.

The mixture feed of line 355 is directed into a separator 356. The separator 356 will be operated as a glycol decanter, with glycerol, glycol or other immiscible materials removed via line 357, and recycled into reactor 350. The crude ester phase, comprising propylene glycol monoesters and diesters, as well as various glycerides, is shown removed from separator 356 through line 360. It is directed into stripper 361, for removal of volatiles. Stripper 361, of course, is an optional step.

The mixture of esters, removed from the stripper 361 is shown directed via line 362 into optional wash 363. In wash 363, a relatively polar solvent, for example water or a mixture of water and ethanol, can be applied to remove highly polar impurities from the mixture of various esters. A similar wash was described in connection with FIG. 2, at 138.

The esters are shown removed from water wash 363 via line 364. They are eventually directed via line 365 into extractor 370. In extractor 370, they are treated with a countercurrent extractant phase directed in via line 371, with the extractant, containing a preferred monoester phase therein, primarily, removed via line 372. It is foreseen that a preferred extractant introduced via line 371 would be an aqueous alcohol mixture, preferably water/ethanol containing, by weight, 20–40% water and 60–80% alcohol.

The raffinate from extractor 370 is shown removed via line 375. The raffinate would generally contain diesters and triesters (contaminating esters), as well as the propylene glycol monoesters (target esters). That is, preferably the extraction which occurs in extractor 370 is tuned so that the material removed via line 372 is high in glyceride monoester content (one of the contaminating esters when PGME's are the target ester), but low in propylene glycol monoester (target ester) and diester content (contaminating ester), as well as low in diglyceride and triglyceride content (also contaminating esters).

The monoglycerides removed via line 372 are directed into the second extractor 386, wherein they are washed with a triglyceride wash via line 387 and are removed to monoglyceride recovery via line 388. This may be generally as described above in connection with FIGS. 1 and 2, for monoglyceride recovery (Stage III). It is noted that the triglyceride phase is shown removed from extractor 386 via line 389 and it is mixed with the crude phase to be purified, introduced via line 364.

Thus far, the arrangement of FIG. 5 is generally as described above in connection with FIGS. 1 and 2. Similar conditions and equipment can be used.

Turning now to the phase removed via line 375, which contains the desired propylene glycol monoester therein, as well as contaminating diester and variant glyceride diesters and triesters. It is shown directed via line 375 into line 395, and ultimately into extractor 396. In extractor 396, it is extracted with an extractant phase introduced via line 397, with raffinate removed via line 398 and extractant phase removed via line 399. The extractant introduced via line 397 would generally comprise an aqueous alcohol mix, preferably a mixture of water and ethanol as follows: 5–30% water (by wt.); and, 70–95% alcohol (by wt.).

In general, the extractant will be tuned for preferred or preferential removal of the propylene glycol monoester, relative to various contaminating diesters and triesters. This can be accomplished by adjusting: the water/alcohol content; flow rates; and, number of extraction stages.

Still referring to FIG. 5, the extractant phase, purified in propylene glycol monoester content relative to other contaminants, is directed into the second separator or wash equipment 405, via line 399. Within extractor 405, the material is treated with a triglyceride wash introduced via line 406. The raffinate is removed via line 407, and is directed into line 395. The propylene glycol monoester (target ester) containing phase is removed from extractor 405 via line 410, and is directed to propylene glycol monoester isolation (recovery), for example by the various purification techniques described above in connection with FIG. 1, for monoglyceride isolation (recovery).

Still referring to FIG. 5, at 415 a separator for the raffinate of line 398 is shown. Line 416 can be used to introduce water, for example, into the separator 415, in order to reduce the alcohol content of the raffinate, similarly to separator 70, FIGS. 1 and 2. The water wash is shown removed via line 417, with the remaining organic phase, containing triglyceride and various diesters (contaminating esters) directed via line 420, through recycling, into reactor 350. An auxiliary triglyceride feed is shown at line 421.

It is anticipated that a system of this type could be used to give propylene glycol monoester compositions with purity of greater than 85%, by weight; and preferably greater than 90%, by weight; based on total ester content.

VI. Some Advantageous Operations; Products

In general, the processes and techniques described herein result in purification of target esters as food compositions. These materials can be used as food additives, to advantage in food mixes. Typical target esters isolated according to the present invention will be monoesters such as monoglycerides or propylene glycol monoesters; or, diesters such as diglycerides.

In general, selected target esters according to the present invention will have wide application in the food industry. Many of them possess characteristics rendering utility in connection with the following:

1. Operation as an emulsifier.
2. Operation as a starch complexing agent.
3. Operation to reinforce protein.
4. Operation in aeration and to stabilize foam.
5. Operation to modify fat crystallization tendencies.

More specifically, many of the target esters that can be isolated according to the present invention will be effective as emulsifiers in food mixes. They can be used, for example, to stabilize water-in-oil emulsions (for example in the generation of margarines or low calorie spreads); or, in the stabilization of oil-in-water emulsions (for example in milk emulsions or salad dressings). Monoglycerides, propylene glycol esters, and modified monoglycerides have been widely utilized in this manner. Generally what is required is an emulsifying (or emulsion-stabilizing) effective amount of the agent, to achieve the desirable effect. While the most desirable amount will differ depending upon the particular composition involved, in general the amounts of isolated target ester materials used according to the present invention that will be preferred or effective, will be similar to amounts used with respect to emulsifying agents in previous compositions, according to known techniques. Some examples are provided hereinbelow.

With respect to operation as a starch complexing agent, in general it has been observed that especially monoglycerides have a starch complexing effect. In operation, they are mixed into such food mixes or dough formulations and have the effect of providing some crumb conditioning and anti-sticking properties. In general, their utilization will involve providing a starch complexing effective amount in a dough composition. They may similarly be used in food mixes for pasta products and potato products, two other food products with high starch compositions, for related desirable features. Examples of the use of monoglycerides in "starch complexing effective amounts" are provided hereinbelow.

Another manner in which target esters according to the invention may be used is in doughs or as dough conditioning agents, due to their properties to reinforce proteins. Typical preferred target esters for accomplishment of this are the diacetyl tartaric acid esters of monoglyceride and ethoxylated monoglycerides and ethoxylated diglycerides. In general as a result of protein interaction, they have been found, when added to bread doughs for example, to provide for higher bake volume and desirable or preferential texture. In general, what is required is a dough conditioning effective amount or protein interaction effective amount of the additive, to achieve the desirable improvement in property. Typical applications to achieve this would be a use at about 0.1–0.6%, by wt., based on the bread dough flour weight.

Also as indicated above, certain selected target esters according to the present invention are desirable as aerating agents and foam stabilizers. Use as foam stabilizers would typically involve addition in compositions for generation of whipped toppings made from dairy cream and imitation cream. When used in this manner, they bring about destabilization of fat globules to promote the formation of a good and stable foam. In general, target esters utilizable for this comprise either the monoglycerides, modified monoglycerides or propylene glycol monoesters. Typical preferred ones for this use are propylene glycol monoesters, lactylated monoglycerides and acetylated monoglycerides. Typical amounts of use in whipped toppings are provided hereinbelow.

As to utilization as an aerating agent, typical applications involve use in various batters, for example cake batter, so that when whipped, it generates higher volume due to aeration. Monoglycerides are among the preferred target esters, for use in these applications. Typical amounts are provided hereinbelow.

Finally, it was indicated above that target esters will in some instances be used to modify fat crystallization tendencies. For example, the typical applications will be as additives to monoglycerides (i.e., the target ester would be a propylene glycol ester or modified monoglyceride which is then added to a monoglyceride to affect its crystallization form or tendencies), or to modify crystallization tendencies in such materials as chocolates containing cocoa butter substitutes, to affect the crystallization tendency of the substitute. Typical amounts effective to accomplish these will be varied depending upon the specific components; however, generally not more than about 2%, by wt., in the food composition will be needed for desirable effects.

Another use of various target esters isolated according to the present invention is in shortenings. In general, shortenings are mixtures of edible fats processed for certain desirable characteristics, for example, preferred melting profiles or solid fat indices. Typical target esters to be added to such compositions will be the monoglycerides, the diglycerides and the propylene glycol monoesters. These materials will be usable in both all purpose shortenings and also specialized shortenings such as shortenings targeted to specific bakery segments. The amounts will be varied, depending on the specific shortening formulation and use. In general, amounts similar to those used in conventional shortenings will be acceptable and desirable. Relative to other uses of target esters described above, the amounts used in shortenings may be very high.

Sometimes processes which involve distillation of monoesters such as monoglycerides or propylene glycol monoesters, are associated with the generation of "off tastes" and/or "off aromas" in the final product. The specific source of these off flavors or off aromas is not presently known. However, it seems to be associated with the conduct of distillation processes, i.e., processes that concern heating mixtures containing the monoglyceride (or propylene glycol monoester) of interest until they vaporize under the distillation conditions, typically 240° C. Methods according to the present invention can be conducted in overall process systems wherein no distillation of the monoglyceride product (PGME product or other ester product isolated) occurs anywhere in the system, and in which, after Stage II is begun, the monoester (or other ester) to be purified is never subjected to temperatures above about 140° C., and typically not above 100° C. This can lead to the generation of product not possessing the same extent of "off flavor" or "off odor" characteristic sometimes associated conventional processing. In addition, by avoiding exposure to high temperature, the product may be more shelf stable. The processes of the most preferred systems such as shown in FIG. 1 are systems in which no distillation of the monoglyceride (or PGME) occurs.

In addition, processes according to present invention can be utilized or "tuned" to obtain preferred levels of purity for the target ester. In general, with distillation processes, the upper limit of purification (of monoglycerides) obtained in the commercial practice in the past has been about 3% diglyceride residual. With extraction processes according to the present invention, purifications on the order of less than 5% diglyceride residual, typically less than 3% and often even less than 2% diglyceride residual can be readily obtained, if desired.

Again, in addition to use as an emulsifier in food systems, purified monoglycerides according to the present invention can be used as a starting material for the production of a number of related emulsifiers. For example, acetylated monoglycerides, citric acid esters of monoglycerides, sodium salts of citric acid esters of monoglycerides, diacetyl tartaric acid esters of monoglycerides, and lactic acid esters of monoglycerides are all emulsifiers derived from monoglycerides. It is anticipated that preferred such materials can be prepared from purified monoglycerides according to the present invention.

It is also noted that derivatives of glycerides can be purified from crude mixtures of derivatives using the same techniques described above for isolation of monoglycerides or diglycerides. That is, the general principles of aqueous alcohol extraction and, optionally, providing a triglyceride enriched non-polar counterphase, can be applied to the purification of derivatives. (It is noted that such derivatives are not readily purified by distillation.) It is foreseen that the most suited derivatives to such a process would be the acetylated monoglycerides, citric acid esters of monoglycerides, diacetyl tartaric acid esters of monoglycerides and lactic acid esters of monoglycerides.

Derivatives of target esters can be prepared using general, conventional, techniques. For example, lactic acid esters of monoglycerides are made by reacting lactic acid with the purified monoglycerides. (Of course because lactic acid possesses a free hydroxyl group available for further reaction, dimers and oligomers are possible. Thus with conventional techniques, control of the reaction may be necessary to achieve the desired mix of lactic acid esters.) Citric acid esters can analogously be manufactured by the reaction of citric acid and monoglycerides. Succinylated monoglycerides are generally the succinic acid ester of monoglycerides made from reacting succinic anhydride with monoglycerides. The resulting reaction mix would generally comprise monoglycerides, and mono- and di- substituted succinylated monoglycerides.

Acetic acid esters of monoglycerides are generally manufactured from a reaction of monoglyceride with acetic anhydride, followed by distillation of acetic acid from the resulting mixture of monoglyceride, and mono- and di-substituted acetylated monoglycerides. Alternatively, they are made by the interesterification of triacetin, triglycerides and glycerol, which would lead to a complex mixture of mono-, di- and triglycerides to be purified using the techniques described herein.

Diacetyl tartaric acid esters of monoglycerides are generally formed by reaction of diacetyl tartaric acid anhydride and the monoglyceride. Again, a complex mixture can form if rearrangement occurs, but the mixture can be appropriately purified using the techniques described herein. Similarly to the other derivatives described above, ethoxylated derivatives can be made using conventional techniques.

As indicated generally above, derivatives of monoglycerides would have a variety of uses in the food industry, either used alone or in combination to provide emulsion stabilization, to provide improved aeration and foam stabilization, to form complexes with starch and prevent staling and sticking, to strengthen dough to retain its rise, and to prevent changes in crystal structure during storage. Useful levels generally range from 0.5 wt % up to 8 wt %, depending on the product and application. The purified monoesters provided by the present invention are believed to be suitable replacements for distilled monoesters at about the same use levels. In addition, the monoesters of the present invention may be a cost effective replacement, in some instance, for crude monoesters and the use level would be based on comparable amount of monoester.

The monoesters of the present invention would be provided in a similar form to the existing products, as a liquid or solid, bulk, powder, flake, 50 lb. cube, dry or hydrated, with or without the appropriate antioxidants, crystal habit modifiers, and carriers.

Processes according to the present invention can be operated in generally preferred, economic, manners, due to the recycling capabilities discussed above with respect to FIGS. 1–5. Also pressurized conditions, and thus for many steps equipment associated with pressurized conditions, can be avoided. Finally, heating target ester material to in excess of 140° C. is generally avoided, leading to an energy savings, and reduced formation of oxidation products and/or off-flavors.

Processes according to the present invention are well developed for utilization in the preparation for a variety of monoglycerides or monoglyceride mixtures. The processes are not sensitive to whether or not the triglyceride materials fed into the system are pure, and whether they are liquid, solid or a mixture thereof. The separations will be effective under any of these conditions, and thus the techniques are widely applicable.

In general, the processes described herein can be performed using triglycerides of fatty acids or fatty acid esters of any desired degree of saturation, depending on the desired functionality of the final product. Typically, products can be made with any desired degree of hydrogenation, specified by the iodine value (IV), ranging from IV=2 or less, to IV=90 or higher, if desired. Products with a low IV (i.e., less than 5) are frequently used as emulsifying agents in margarine, cake shortening and coatings for candies. They are also used in baked products or in potato products. In these latter applications, the ability to form a complex with amylose starch is useful to provide antistaling, crumb conditioning agent, and in whipped toppings where the foam stabilization properties are useful. Low IV monoglycerides are also frequently used as starting points in the production of other emulsifier products, such as acetylated monoglycerides, citric acid esters of monoglycerides, sodium salts of citric acid esters of monoglycerides, diacetyl tartaric acid esters of monoglycerides, and lactic acid esters of monoglycerides.

The high IV (greater than 40) products are typically used when a softer or more liquid product is required. For example, an IV 40 monoglyceride might be useful for icing or soft margarine, and IV 70 or IV 90 monoglycerides might be used when even softer consistency is desired.

In general, processes according to the present invention are designed to be operated, if desired, above the melting point of the materials in question, thus treating the product essentially in a liquid state. In general it is believed that this will give a process which is readily adapted for a variety of oils of differing degrees of saturation. The separation is driven primarily by functionality, especially the balance between polar and nonpolar moieties. Because of this, the processes are believed to be applicable to either mixtures of oils of different IVs or to oils of intermediate IV, which may inherently include a variety of compounds, operating with or without causing an undesired fractionation of the material on the basis of its degree of saturation. Processes which rely on melting point differences, such as fractional crystallization, are not believed to be as robust in this sense. Instead, the separation will depend strongly on the IV of the material, because saturation strongly influences melting point.

With respect to iodine value (IV), it is noted that this measure of unsaturation can be measured using standard techniques, such as AOCS method #CD1B87, "The iodine value of fats and oils using the cyclohexane method", incorporated herein by reference.

It is noted that the techniques described herein can be applied to the purification of other polyhydric alcohols, besides glycerol or propylene glycol, which have been partially esterified with fatty acids. For example, to separate sorbitan mono-esters from sorbitan di- or tri-esters, or to separate, at least partially, complex mixtures of polyglycerol esters of fatty acids. Related techniques may also be applied to ethyoxylated products, such as polyoxyethylene sorbitan monoesters or ethoxylated monoglycerides.

VII. Preferred Equipment

From the following examples of certain preferred equipment, general principles of the present invention and its application will be even further understood.

For example, for the primary and secondary extractors equipment such as: mixer/settler tanks; pulsed columns; baffle columns; reciprocating plate columns; Podbielniack centrifugal contactors; rotating disc contactor columns; and similar devices may be used. Such equipment provides the required cycles of intimate contacting between phases, with follow-up phase separation.

For the various separators, a low shear mixing system is preferred to reduce the likelihood of emulsion formation.

VIII. Diglyceride Isolation

Diglycerides may be used as components in shortening, in some instances at levels of 30% or more, and as fat replacers. As fat replacers, they can be substituted for triglycerides, normally at less than 1 part by weight for each part triglyceride removed. Some products in which they may be useful are low fat sour cream, fat replacement in pie crusts and baked goods, icings, and frozen ice cream or other frozen dairy products.

The systems described in FIGS. 1–4 can be used to isolate a purified diglyceride stream (i.e., in these applications, the diglycerides are the target esters).

In general, the raffinate from the extraction of monoglycerides, in line 52, would comprise typically 60%, or less, by weight diglycerides (and 3% or less, typically 1% or less, by wt., monoglycerides), of the total glyceride component. For example, in the hypothetical commercial system described hereinbelow, the raffinate phase is reported as comprising 2,150 lbs./hr. of triglyceride, 1,330 lbs./hr. diglyceride and 20 lbs/hr. monoglyceride, with small amounts of water and ethanol. The water and ethanol, of course, can be removed by vacuum stripping. Thus, the composition of the fat components (glycerides) by weight, based on total glycerides content, would be about 61% triglyceride, 38% diglyceride and less than 1% (0.6%) monoglyceride. Of course, alternate raffinate compositions could be obtained with the system previously described, with each generally characterized by a high ratio of diglyceride to monoglyceride, in a triglyceride carrier. That is, the majority of the composition, by weight, would comprise triglyceride, with the remainder comprising diglyceride and having a high diglyceride to monoglyceride ratio. Typical diglyceride to monoglyceride ratios, by weight, in this material of about 20:1 to 100:1 could be readily achieved, with the processing described herein. If desired, even higher ratios could be obtained by increasing the extraction of monoglyceride in the extractor 50, using more stages if appropriate. There is no theoretical limit to the ratio of diglyceride to monoglyceride in these compositions, and it is foreseen that ratios of 500:1 would generally be practical and achievable with available equipment.

Of course the relative amounts of diglyceride (target ester) and triglyceride (contaminating ester) would depend upon the composition of the initial crude monoglyceride and the amount of triglyceride extracted and added. Diglyceride contents of about 20–60%, by weight based upon total glycerides content, would be typical for the raffinate in line 52, FIGS. 1–3. Products in this range of compositions would be useful where blends of triglycerides and diglycerides, with a minimum of monoglycerides, i.e., less than 1% by wt., are desired. Such compositions would not be readily obtainable through normal glyceride ester productions, where expected compositions would generally always contain at least 1% monoglyceride if the diglyceride content was 20% or more.

Figure 3:
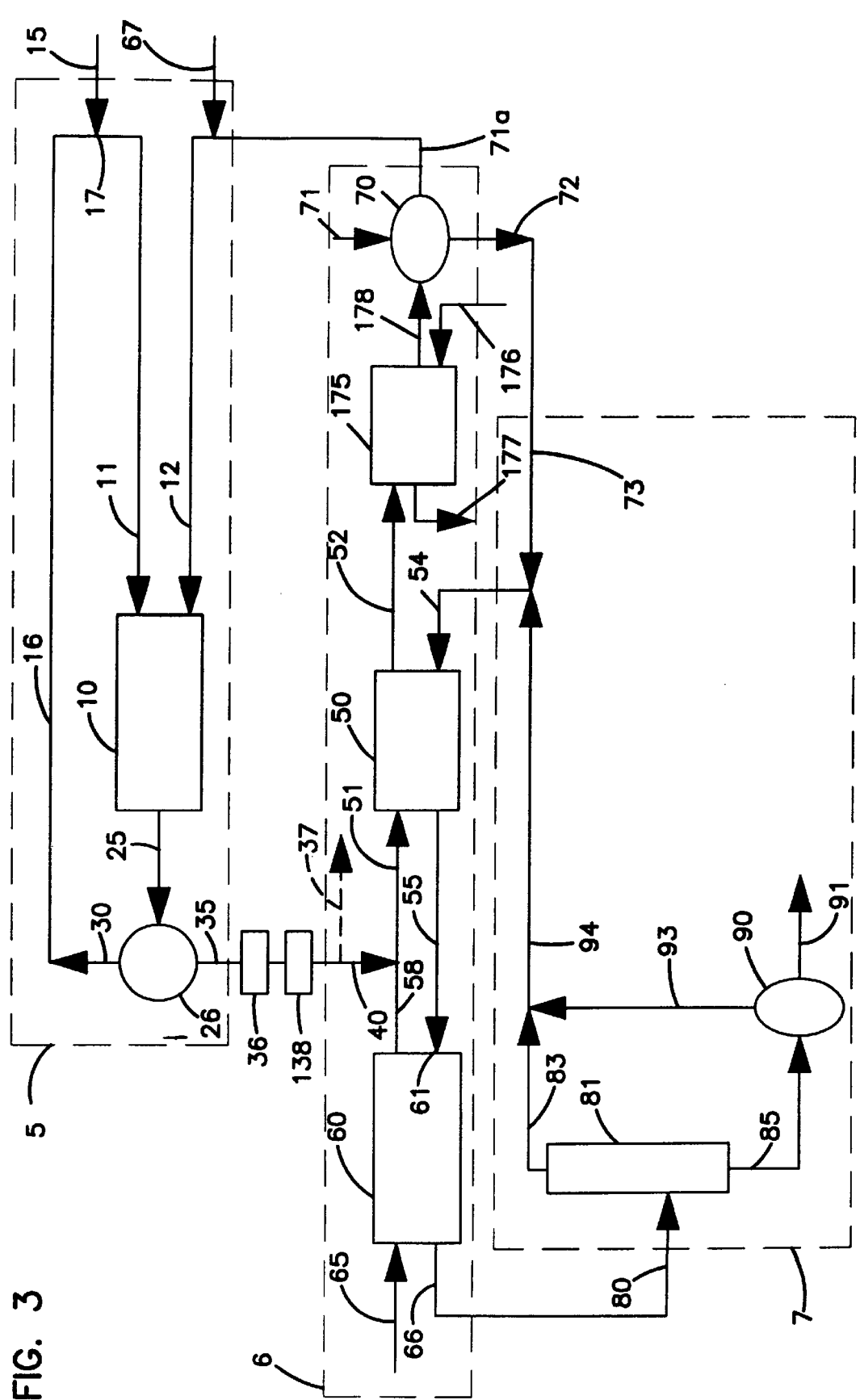
FIG. 3 is a schematic presentation of a process and equipment for practice of the process described in connection with FIG. 2, FIG. 3 also including process steps and equipment for isolation of a purified diglyceride stream.

Compositions containing greater than 50% diglycerides, and indeed greater than 60% diglycerides, by weight, can be obtained. For example, the raffinate from the extraction of the process shown in FIG. 1, i.e., removed via line 52, can be extracted with a second polar phase extractant. Such a system is shown in FIG. 3. FIG. 3 is generally analogous to FIGS. 1 and 2, with like reference numerals referring to the same or analogous steps and equipment. In FIG. 2, the raffinate removed via line 52 from extractor 50 is directed into a second extractor 175. Extractant feed is shown fed in via line 176 and removed via line 177. Via line 177, then, an extractant phase containing purified diglycerides (target ester) would be removed. It could be directed to a recovery, not shown, generally comprising appropriate equipment for removal of solvent, etc. The raffinate from extractor 175 is shown removed via line 178 and directed into separator 70.

It is foreseen that a preferred extractant composition would be about 5–30%, by weight, water with the balance ethanol, although other ratios of water and either ethanol or other alcohols could be used. This would create a generally polar solvent, in which the diglycerides (target ester) would be soluble in preference over the triglycerides (contaminating ester). In general, the extractant would contain less water, as a weight percent, than the extractant used to remove the monoglycerides, in order to improve loading. The extraction would generally, and preferably, be conducted in a countercurrent extractor such as extractor 175. Selectivities for extraction of diglycerides from a diglyceride/triglyceride mixture, in the substantial absence of monoglycerides, are not available. However, based on selectivities calculated from compositions shown in the Examples herein, a product of composition of greater than 60 wt. % diglyceride with the balance triglyceride, and with less than about 1% by wt. monoglyceride, is considered readily feasible. If higher purities of diglyceride are desired, a diluent could be added to the nonpolar phase to improve the selectivity of DG/TG. For example, in the description herein of Example 2, addition of hexane eliminated triglyceride in the polar phase. An analogous approach could be used in extractor 175.

Loading of the diglyceride in the polar phase will be reduced, in the presence of the diluent, however. The technique described appears capable of readily generating diglyceride concentrations of 60–80 wt. %, and perhaps as high as 90 wt. %. However, due to the low extraction coefficient for diglycerides and aqueous alcohol (typically less than 0.5), relatively high amounts of solvent feed via line 176 may be needed.

Figure 4:
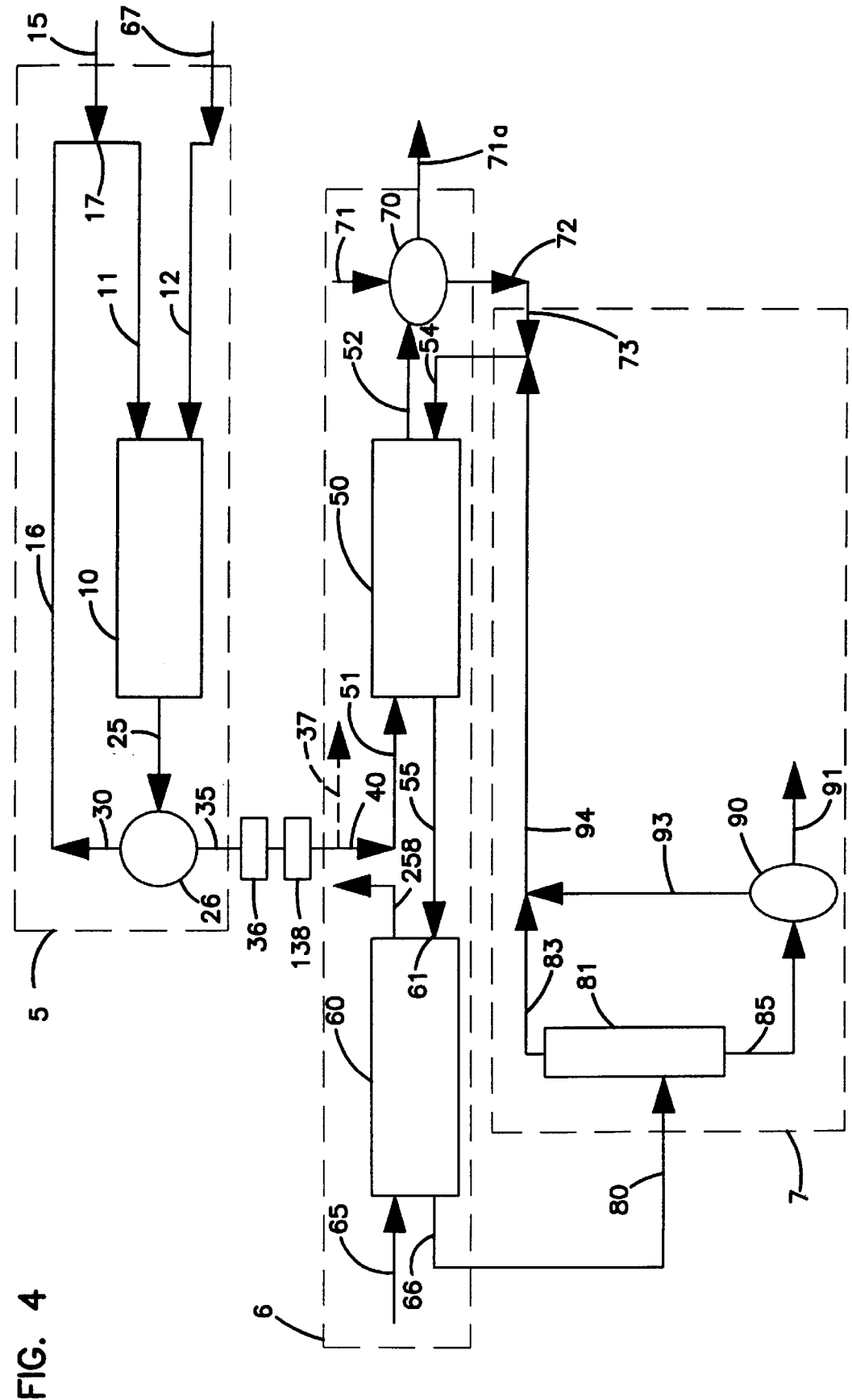
FIG. 4 is a schematic presentation of a process and equipment for practice of an alternative process to that described in connection with FIG. 3.

An alternate approach is shown in FIG. 4. FIG. 4 differs from FIGS. 1 and 2 in that line 58 is absent, and now line 258, from extractor 60, would be directed to reactor 10 rather than extractor 50. It is foreseen that the process of this figure is particularly well suited to purification of mixtures containing at least four times as much diglycerides as triglycerides, by wt.; and that the monoglycerides extraction would be tuned to removal of at least 85%, preferably at least 90%, and in some instances greater than 95%, by wt., of monoglycerides in the composition, based on total glycerides weight. Also preferably in a process according to FIG. 4, the extraction in extractor 50 is tuned so that less than 20%, by wt., of the diglycerides are extracted into the extractant.

Thus, FIG. 4 shows an alternate scheme using just two extractors for the production of both a monoglyceride stream and a diglyceride stream. The diglyceride stream is produced without need to extract it into a polar phase. In FIG. 4, the crude monoglyceride, preferably containing low triglyceride, is extracted in a primary extractor with an aqueous alcohol polar phase, without addition of triglyceride. Conditions in the extractor are set to extract essentially all of the monoglyceride and only a portion of the diglyceride. For example, if a 10:1 selectivity for mono/diglycerides is available, then by adjusting the flow rates and using a large number of stages (6 or more equilibrium stages), it should be possible to extract any arbitrarily large fraction of the monoglycerides, while extracting only about 12% of the diglycerides. The raffinate would contain a high concentrate of diglycerides, moderate concentration of triglycerides, and a low concentration of monoglycerides, and would be suitable as a diglyceride concentrated product. A typical product, starting from a crude monoglyceride composition of 65 wt. % monoglyceride, 31 wt % diglyceride, and 4 wt. % triglyceride, will contain about 80–88 wt. % diglyceride, 0–9 wt. % monoglyceride, and 11–13 wt. % triglyceride. The ultimate purity would be limited by the triglyceride content of the crude monoglyceride feed. However, for products in which this would not be an issue, the approach described in connection with FIG. 4 would be a preferred method, as it requires just two extractors and does not require solubilizing the diglycerides into an aqueous solvent.

The polar phase, loaded with monoglycerides and some of the diglycerides, would be directed to a second extractor and contacted countercurrently with a triglyceride stream. This would produce a polar phase with a high purity monoglyceride. The triglyceride phase, now containing some diglyceride, would preferably be sent to a feed inlet of a crude monoglyceride production unit, preferably after washing and/or stripping to remove water and alcohol.

IX. Experimental

EXAMPLE 1
Comparison of Extraction Using Aqueous Isopropanol with Either Triglyceride Oil or Hexane as a Carrier Phase Single stage, equilibrium experiments were performed by mixing together aqueous isopropanol (containing either 15 or 25% water by volume), a less polar carrier phase of either IV 78 corn oil or hexane, and crude monoglycerides. The samples were made up into test tubes, heated in a temperature controlled water bath, and mixed. After mixing, the samples were allowed to stand in the water bath for at least 1 hour before sampling. Aliquots were taken of each phase, for the systems which formed two phases, and the aliquots were analyzed by gas chromatography after being evaporated at 110° C. in flowing nitrogen. The monoglyceride content for the samples in the table below were 2 grams crude monoglyceride per 10 ml of combined solvent. Samples were also made at 4 grams crude monoglyceride per 10 ml of combined solvent, but these did not generally result in more than a single phase. The solvents were added at a volume ratio of polar solvent to less polar solvent of either 1/1 or 2/1. The initial composition of the crude monoglycerides was approximately 60%/35%/5% by weight of monoglyceride/diglyceride/triglyceride. The selectivity for the monoglyceride over diglycerides and selectivity for monoglycerides over triglycerides are also reported.

Hexane was shown to be unsuitable for use as a second phase. Other hydrocarbons are expected to behave similarly.

EXAMPLE 2
Comparison of Extraction using Aqueous Ethanol with Either Triglyceride Oil or Hezane as Carrier Phase Single stage, equilibrium experiments were performed by mixing together aqueous ethanol (containing either 25 or 35% water by volume), a less polar carrier phase of either IV 78 corn oil or hexane, and crude monoglycerides. The samples were made up into test tubes, heated in a temperature controlled water bath, and mixed. After mixing, the samples were allowed to stand at least 1 hour before sampling. Aliquots were taken of each phase, for the systems which formed two phases, and the aliquots were analyzed by gas chromatography after being evaporated at 110° C. in flowing nitrogen. The monoglyceride content for the samples in the table below were 2 or 4 grams crude monoglyceride per 10 ml of combined solvent. The solvents were added at a volume ratio of polar solvent to less polar solvent of either 1/1 or 2/1. The initial composition of the crude monoglycerides was approximately 60%/35%/5% by weight of monoglyceride/ diglyceride/triglyceride. The IV of the crude monoglycerides was approximately 70. The selectivity of the polar phase for monoglyceride over diglycerides, selectivity for monoglyceride or triglyceride, and the partition coefficient for the monoglycerides are also

TABLE I

Test results over diglycerides oil as less polar phase.

| Temp (C.) | Water vol % | [1]Polar/ Non-polar | [2]MG, wt % polar | [3]DG, wt % polar | [4]TG, wt % polar | [5]MG, wt % non-polar | [6]DG, wt % non-polar | [7]TG, wt % non-polar | [8]Selectivity MG/DG | [9]Selectivity MG/TG |
|---|---|---|---|---|---|---|---|---|---|---|
| 45 | 15 | 1 | 42   | 24   | 34   | 11   | 17   | 72   | 2.7  | 8.1  |
| 45 | 15 | 2 | 43.6 | 15.6 | 40.8 | 12.6 | 11.4 | 76   | 2.5  | 6.4  |
| 60 | 15 | 1 | 48.8 | 13.9 | 37.3 | 8.6  | 10.1 | 81.2 | 4.1  | 12.4 |
| 60 | 15 | 2 | 31   | 13.7 | 55.3 | 13.1 | 12.1 | 74.8 | 2.1  | 3.2  |
| 45 | 25 | 1 | 64   | 21   | 15   | 8    | 16   | 76   | 6.1  | 40.5 |
| 45 | 25 | 2 | 64.3 | 13.3 | 22.4 | 9.7  | 10.4 | 79.9 | 5.2  | 23.6 |
| 60 | 25 | 1 | 75.1 | 11.4 | 13.5 | 9    | 14.1 | 76.8 | 10.3 | 47.5 |
| 60 | 25 | 2 | 66.8 | 16.9 | 16.2 | 10   | 14.3 | 75.7 | 5.7  | 31.2 |

[1]Polar/non-polar is volume ratio of polar solvent to less polar solvent; i.e., water and isopropanol mix/added triglycerides.
[2]Monoglyceride wt % (based on total weight glycerides) in polar phase.
[3]Diglyceride wt % (based on total weight glycerides) in polar phase.
[4]Triglyceride wt % (based on total weight glycerides) in polar phase.
[5]Monoglyceride wt % (based on total weight glycerides) in non-polar phase.
[6]Diglyceride wt % (based on total weight glycerides) in non-polar phase.
[7]Triglyceride wt % (based on total weight glycerides) in non-polar phase.
[8]Selectivity in this column is calculated from (MG wt % in polar phase + DG wt % in polar phase) + (MG wt % in non-polar phase + DG wt % in non-polar phase).
[9]Selectivity in this column is calculated from (MG wt % in polar + TG wt % in polar phase) + (MG wt % in non-polar phase + TG wt % in non-polar phase).

Test results using hexane, under the same conditions, resulted in single phase systems or in two phase systems with selectivity near 1, yielding no purification of the crude monoglycerides.

This example shows the usefulness of the system aqueous isopropanol/triglyceride for obtaining purification of monoglycerides. The selectivity of monoglyceride to diglyceride is sufficient, but the selectivity of monoglyceride to triglyceride is lower than desired. The selectivity is higher at higher water concentration, and the preferred water content for use with isopropanol is 25 vol % or greater.

shown. In Tables II and III, the reports for the experiments are shown and analogous headings to those used in Table I have analogous meanings.

This example shows the system aqueous ethanol/ triglycerides possesses the beneficial features of high monoglyceride to diglyceride selectivity, high monoglyceride to triglyceride selectivity, and a high extraction coefficient (corresponding to high loading of the extractant phase). The aqueous ethanol/hexane system has good selectivity, but very low extraction coefficients (low loading of the extractant phase).

TABLE II

Test Results using Triglyceride Oil as Less Polar Phase

| Temp °(C.) | Water vol % | Polar/ less polar | MG, wt % polar | DG, wt % polar | Tg, wt % polar | MG, wt % less polar | DG, wt % less polar | TG, wt % less polar | Fat g/ml in polar phase | Fat g/ml in less polar phase | [1]Selectivity MG/DG | [2]Selectivity MG/TG | [3]Partition coefficient K (mono) |
|---|---|---|---|---|---|---|---|---|---|---|---|---|---|
| 2 g/10 ml | | | | | | | | | | | | | |
| 45 | 25 | 1 | 83.1 | 9.1 | 7.8 | 9 | 11.6 | 79.4 | | | 11.8 | 94 | |
| 45 | 25 | 2 | 82.7 | 13.7 | 3.7 | 10.1 | 15.4 | 74.5 | 0.07 | 0.44 | 9.2 | 165 | 1.35 |
| 60 | 25 | 1 | 86.8 | 8.4 | 4.8 | 9.5 | 12.2 | 78.4 | | | 13.3 | 149 | |
| 45 | 35 | 1 | 81.6 | 9.3 | 9.1 | 12.1 | 11.8 | 76.1 | 0.1 | 0.64 | 8.6 | 56 | 1.03 |
| 60 | 35 | 2 | 89 | 7.4 | 3.6 | 11.8 | 14.9 | 73.3 | 0.12 | 0.91 | 15.2 | 164 | 0.99 |
| 4 g/10 ml | | | | | | | | | | | | | |
| 45 | 25 | 1 | 66.1 | 16 | 18 | 20.5 | 16.9 | 62.6 | 0.22 | 0.59 | 3.4 | 11 | 1.2 |
| 45 | 35 | 2 | 81.1 | 13.1 | 5.8 | 32.8 | 21.1 | 46 | 0.05 | 0.58 | 4 | 20 | 0.21 |
| 60 | 35 | 1 | 82.3 | 10.4 | 7.3 | 38.2 | 26.5 | 35.3 | 0.07 | 0.74 | 5.5 | 11 | 0.21 |

[1]In this column, selectivity is for MG over DG.
[2]In this column, selectivity is for MG over TG.
[3]In this column, the partition coefficient K is wt. fraction MG polar/wt. fraction MG in less polar phase.

TABLE III

Results Using Hexane As Less Polar Phase

| Temp (C.) | Water, vol % | Polar/ Less polar | MG, wt % polar | DG, wt % polar | Tg, wt % polar | MG, wt % less polar | DG, wt % less polar | TG, wt % less polar | Fat, g/ml polar | Fat, g/ml less polar | Selectivity MG/DG | Partition coefficient, K (mono) |
|---|---|---|---|---|---|---|---|---|---|---|---|---|
| 2/10 mg | | | | | | | | | | | | |
| 45 | 25 | 1 | 95.3 | 4.7 | 0 | 59.3 | 36.3 | 4.3 | — | — | 12.4 | — |
| 60 | 25 | 1 | 92.7 | 7.3 | 0 | 58.8 | 35.5 | 5.7 | — | — | 7.7 | — |
| 60 | 25 | 2 | 78.6 | 20.4 | 1 | 58 | 36.4 | 5.6 | 0.07 | 0.64 | 2.4 | 0.14 |
| 45 | 35 | 2 | 93.6 | 6.4 | 0 | 58.5 | 35.8 | 5.7 | 0.01 | 0.19 | 9 | 0.04 |
| 60 | 35 | 1 | no data | no data | no data | 59.5 | 35.2 | 5.3 | 0.01 | 0.43 | — | <0.03 |
| 4/10 mg | | | | | | | | | | | | |
| 45 | 25 | 2 | 83.2 | 16.8 | 0 | 58.4 | 35.6 | 6.1 | 0.02 | 0.22 | 3 | 0.1 |
| 60 | 25 | 1 | nd | nd | nd | 59.4 | 35.3 | 5.3 | 0.01 | 0.47 | — | <0.05 |
| 45 | 35 | 1 | 87.8 | 12.2 | 0 | 60.2 | 35 | 4.7 | 0.01 | 0.26 | 4.2 | 0.03 |
| 60 | 35 | 2 | 84.1 | 15.9 | 0 | 58.4 | 36.2 | 5.4 | 0.04 | 0.68 | 3.3 | 0.09 |

EXAMPLE 3
Extraction Using Aqueous Methanol and Triglyceride

Single stage, equilibrium experiments were performed by mixing together aqueous methanol (containing either 5 or 10% water by volume), a less polar carrier phase of IV 40 soybean oil, and crude monoglycerides. The samples were made up into test tubes, heated in a temperature-controlled water bath, and mixed. After mixing, the samples were allowed to stand at least one hour before sampling. Aliquots were taken of each phase, for the systems which formed two phases, and the aliquots were analyzed by gas chromatography after being evaporated at 110° C. in flowing nitrogen. The monoglyceride charge for the samples in the table below were 1 or 2 grams crude monoglyceride per 10 ml of combined solvent. The solvents were added at a volume ratio of polar solvent to less polar solvent of 2/1. The initial composition of the crude monoglycerides was approximately 60%/35%/5% by weight of monoglyceride/diglyceride/triglyceride. The IV of the crude monoglycerides was approximately 70. The selectivity of the polar phase for monoglyceride over diglycerides, the partition coefficient for the monoglycerides, and the selectivity for monoglycerides over triglycerides are also shown. The results are reported in Table IV. In Table IV analogous headings to those used in Table I have analogous meanings.

The example shows the high selectivity (monoglyceride over diglyceride and monoglyceride over triglyceride) and high extraction coefficient (high loading of the extractant phase) for the aqueous methanol/triglyceride system. It appears to be a very feasible system.

TABLE IV

Results Using Aqueous Methanol and Triglyceride

| Temp (C.) | Water vol % | Loading (crude mono per 10 ml solvent) | MG, wt % polar | DG, wt % polar | TG, wt % polar | MG, wt % less polar | DG, wt % less polar | TG, wt % less polar | Fat, g/ml polar | Fat, g/ml less polar | Selectivity MG/DG | Partition coefficient K (mono) | Selectivity MG/TG |
|---|---|---|---|---|---|---|---|---|---|---|---|---|---|
| 60 | 5 | 10 | 89.7 | 10.3 | 0 | 6.3 | 9.3 | 84.4 | 0.08 | 0.67 | 12.9 | 1.68 | — |
| 60 | 5 | 20 | 83.4 | 13.3 | 3.3 | 8.7 | 13.4 | 77.9 | 0.14 | 0.78 | 9.7 | 1.68 | 226 |
| 60 | 10 | 10 | 95 | 5 | 0 | 4.7 | 7.1 | 88.2 | 0.06 | 0.74 | 28.7 | 1.51 | — |
| 60 | 10 | 10 | 82.3 | 7.5 | 10.2 | 14 | 14.9 | 71.1 | 0.11 | 0.82 | 11.7 | 0.8 | 41 |

EXAMPLE 4
Evaluation as Possible Use of Aqueous Butanol with Hexane

Crude monoglycerides (2 gm, IV 70) was weighed into test tubes and 5 ml of a mixture of 88 vol % butanol and 13 vol % water was added. The samples were gently heated to dissolve the crude monoglycerides. 5 ml of hexane was added to the solution and the phases were mixed by gentle shaking. The tubes were placed into a temperature controlled bath (45° C. or 60° C.) for at least one hour. The aqueous butanol/hexane/crude monoglyceride system was observed to form a single phase solution and is not suitable for use in liq-liq extraction processing to purify monoglyceride.

EXAMPLE 5
Use of Aqueous Ethanol with Triglycerides

Crude monoglycerides (IV 70) were weighed into graduated tubes and aqueous ethanol was added (16 vol %, 23 vol %, or 30 vol % water in ethanol). IV 40 soybean oil was added and the samples were heated to 600° C., mixed, and allowed to equilibrate for at least one hour. The charge of crude monoglyceride was either 10, 15, or 20 g/100 ml combined solvent phases, and the ratio of the solvent phases was either 2/1, 3/1, or 4/1 polar/less polar. Aliquots were taken and analyzed for fat content (residue upon evaporation) and for fat composition by GC. The results and calculated values of selectivity (monoglyceride to diglyceride content in polar phase over less polar phase) and extraction coefficient (concentration of monoglycerides in polar phase divided by concentration of monoglycerides in less polar phase) are shown in Table V below. A summary table is also given, showing the mean values for selectivity and extraction coefficient as a function of loading and water content in the aqueous ethanol.

Summary Table

| Charge g/100 ml | Water vol % | Selectivity MG/DG | K (mono) |
|---|---|---|---|
| 10 | 16 | 15 | 2.4 |
| 10 | 23 | 14 | 1.5 |
| 10 | 30 | 23 | 1.0 |
| 15 | 16 | 9 | 1.8 |
| 15 | 23 | 16 | 1.3 |
| 15 | 30 | 12 | 0.8 |
| 20 | 16 | 7 | 2.4 |
| 20 | 23 | 9 | 1.5 |
| 20 | 30 | 10 | 1.4 |
| 20 | 60 | 7 | 0.7 |

The result for 60% water in the aqueous ethanol is from a separate experiment. Water loadings higher than 30 vol % in ethanol tended to produce systems with more than two phases.

The results show the generally favorable characteristics of the aqueous ethanol/triglyceride system. For a given charge, increasing water content resulted in an increased selectivity but decreased extraction coefficient. For a given water content, the selectivity decreases with increased monoglyceride charge. This factor supports the need for a washing section if high loadings are to be used.

TABLE V

| Water in ETOH (vol %) | Charge (g crude) in 10 ml sol | Phase ratio (vol polar/ non-polar) | Phase fat content (g/ml) polar | Phase fat content (g/ml) non-polar | [MG] polar (%) | [DG] polar (%) | [TG] polar (%) | [MG] non-polar (%) | [DG] non-polar (%) | [TG] non-polar (%) | Selectivity MG/DG | Kmono |
|---|---|---|---|---|---|---|---|---|---|---|---|---|
| 16 | 10 | 3 | 0.112 | 0.706 | 81.2 | 14.6 | 4.2 | 5.4 | 12.7 | 81.9 | 13.1 | 2.39 |
| 16 | 10 | 3 | 0.082 | 0.729 | 84.6 | 12.8 | 2.6 | 3.8 | 10.2 | 86 | 17.7 | 2.50 |
| 30 | 10 | 3 | 0.074 | 0.887 | 93.4 | 6.6 | 0.6 | 7.4 | 12.5 | 80.1 | 23.9 | 1.05 |
| 30 | 10 | 3 | 0.055 | 0.769 | 92.6 | 7.4 | 0.0 | 6.7 | 12.3 | 81 | 23.0 | 0.99 |
| 16 | 20 | 3 | 0.194 | 0.759 | 76.0 | 16.7 | 7.3 | 9.2 | 16.5 | 74.3 | 8.2 | 2.11 |
| 16 | 20 | 3 | 0.224 | 0.650 | 69.2 | 20.0 | 10.8 | 8.9 | 13.5 | 77.6 | 5.2 | 2.68 |
| 30 | 20 | 3 | 0.151 | 0.748 | 79.6 | 14.8 | 5.6 | 9.6 | 15.8 | 74.6 | 8.9 | 1.68 |
| 30 | 20 | 3 | 0.116 | 0.774 | 86.3 | 10.6 | 3.1 | 12.2 | 16.6 | 71.2 | 11.1 | 1.06 |
| 16 | 15 | 2 | 0.107 | 0.739 | 80.0 | 15.1 | 4.9 | 5.7 | 12 | 82.2 | 11.2 | 2.03 |
| 16 | 15 | 2 | 0.132 | 0.818 | 77.4 | 17.9 | 4.7 | 5.3 | 11.3 | 83.4 | 9.2 | 2.36 |
| 16 | 15 | 4 | 0.098 | 0.823 | 76.4 | 19.5 | 4.1 | 7.8 | 13.3 | 78.8 | 6.7 | 1.17 |
| 16 | 15 | 4 | 0.108 | 0.763 | 75.0 | 20.9 | 4.0 | 6.1 | 12.2 | 81.7 | 7.2 | 1.70 |
| 30 | 15 | 2 | 0.071 | 0.833 | 90.5 | 9.5 | 0.0 | 9.6 | 11.2 | 79.2 | 11.1 | 0.80 |
| 30 | 15 | 2 | 0.069 | 0.888 | 90.9 | 9.1 | 0.0 | 9.2 | 11.1 | 79.7 | 12.1 | 0.76 |
| 30 | 15 | 4 | 0.065 | 0.705 | 88.9 | 11.1 | 0.0 | 9.7 | 15 | 75.3 | 12.4 | 0.84 |
| 23 | 10 | 2 | 0.049 | 0.729 | 88.6 | 11.4 | 0.0 | 5.8 | 7.6 | 86.6 | 10.2 | 1.02 |
| 23 | 10 | 2 | 0.070 | 0.724 | 87.8 | 10.6 | 1.6 | 5.8 | 7.9 | 86.2 | 11.3 | 1.46 |

TABLE V-continued

| Water in ETOH (vol %) | Charge (g crude) in 10 ml sol | Phase ratio (vol polar/ non-polar) | Phase fat content (g/ml) polar | Phase fat content (g/ml) non-polar | [MG] polar (%) | [DG] polar (%) | [TG] polar (%) | [MG] non-polar (%) | [DG] non-polar (%) | [TG] non-polar (%) | Selectivity MG/DG | Kmono |
|---|---|---|---|---|---|---|---|---|---|---|---|---|
| 23 | 20 | 2 | 0.112 | 0.778 | 86.6 | 13.4 | 0.0 | 10.5 | 12.9 | 76.5 | 7.9 | 1.18 |
| 23 | 20 | 2 | 0.136 | 0.717 | 82.1 | 14.4 | 3.6 | 11.0 | 13.3 | 75.7 | 6.9 | 1.42 |
| 23 | 10 | 4 | 0.058 | 0.880 | 86.7 | 10.4 | 2.9 | 7.7 | 12.1 | 80.2 | 13.1 | 1.0 |
| 23 | 10 | 4 | 0.088 | 0.500 | 84.6 | 9.2 | 6.2 | 4.9 | 11.2 | 83.9 | 21.0 | 2.35 |
| 23 | 20 | 4 | 0.139 | 0.553 | 79.2 | 14.3 | 6.5 | 14.3 | 18.2 | 67.5 | 7.0 | 1.39 |
| 23 | 20 | 4 | 0.127 | 0.691 | 84.9 | 13.5 | 1.6 | 8.4 | 17.5 | 74.1 | 13.1 | 1.85 |
| 23 | 15 | 3 | 0.098 | 0.784 | 90.3 | 9.7 | 0.0 | 7.9 | 11.6 | 80.4 | 13.7 | 1.43 |
| 23 | 15 | 3 | 0.111 | 0.683 | 89.9 | 10.1 | 0.0 | 10.3 | 14.9 | 74.8 | 12.9 | 1.42 |
| 23 | 15 | 3 | 0.102 | 0.893 | 89.6 | 10.4 | 0.0 | 10.0 | 12.6 | 77.4 | 10.9 | 1.03 |
| 23 | 15 | 3 | 0.091 | 0.661 | 92.5 | 7.5 | 0.0 | 7.4 | 14.2 | 78.4 | 23.7 | 1.73 |
| 23 | 15 | 3 | 0.094 | 0.738 | 92.3 | 7.7 | 0.0 | 8.5 | 14.1 | 77.5 | 19.9 | 1.38 |
| 23 | 15 | 3 | 0.099 | 0.768 | 92.3 | 7.7 | 0.0 | 10.6 | 13.9 | 75.5 | 15.7 | 1.12 |

EXAMPLE 6

Equilibrium Distribution at Low Diglyceride Level

A series of experiments was run to determine the equilibrium distribution between mono-, di-, and triglycerides at moderate levels of diglyceride. Mixtures were made up using a triglyceride oil, distilled monoglycerides (IV 70), and aqueous ethanol. The aqueous ethanol was either 16, 23, or 30 vol % water in ethanol. The aqueous ethanol was added in an amount sufficient to give a two phase system. The samples were mixed and equilibrated at about 65° C. Aliquots were removed and the fat content determined by residual weight after evaporation at about 110° C. in flowing nitrogen. The evaporated samples were then derivitized and analyzed by GC to determine the monoglyceride, diglyceride, and triglyceride content. Water was determined by Karl Fisher analysis and found to be about 0–3 wt % of the less polar phase. The ethanol in the less polar phase increased with increasing monoglyceride content. Selectivity of the polar phase for monoglycerides over diglycerides and the monoglyceride extraction factor (concentrations based on weight) are shown in the attached Table VI.

This example shows that as the fat content of the polar phase increases (increased loading) the amount of triglycerides entering the polar phase also increases, eventually limiting the monoglyceride purity. However, even at fat contents of greater than 10 wt % in the polar phase, the triglycerides are relatively low for the aqueous ethanol/ triglyceride system.

TABLE VI

| | Polar phase MG (wt %) | Polar phase DG (wt %) | Polar phase TG (wt %) | Nonpolar phase MG (wt %) | Nonpolar phase DG (wt %) | Nonpolar phase TG (wt %) | Fat content polar phase, Wt % | Fat content less polar phase, Wt % | Selectivity MG/DG | K (mono) wt basis |
|---|---|---|---|---|---|---|---|---|---|---|
| 23% Water | | | | | | | | | | |
| | 95.85 | 1.21 | 2.95 | 0.67 | 1.39 | 97.95 | 3 | 99 | 164.3 | 4.34 |
| | 96.15 | 0.43 | 3.41 | 2.29 | 1.27 | 96.44 | 2 | 98 | 124.0 | 0.86 |
| | 96.82 | 0.79 | 2.39 | 3.27 | 1.31 | 95.42 | 10 | 97 | 49.1 | 3.05 |
| | 98.38 | 0.44 | 1.18 | 4.15 | 1.32 | 94.52 | 5 | 99 | 71.1 | 1.20 |
| | 96.86 | 0.95 | 2.18 | 5.29 | 1.62 | 93.09 | 11 | 96 | 31.2 | 2.10 |
| | 94.2 | 0.45 | 5.35 | 10.15 | 1.05 | 88.8 | 14 | 96 | 21.7 | 1.35 |
| | 88.32 | 1.05 | 10.63 | 13.07 | 1.21 | 85.72 | 25 | 95 | 7.8 | 1.78 |
| | 88.62 | 1.22 | 10.15 | 11.02 | 1.33 | 87.65 | 21 | 96 | 8.8 | 1.78 |
| | 92.4 | 1.18 | 6.42 | 18.63 | 1.31 | 80.06 | 15 | 94 | 5.5 | 0.79 |
| 30% Water | | | | | | | | | | |
| | 94.79 | 0.66 | 4.56 | 2.02 | 1.46 | 96.52 | 6 | 98 | 103.8 | 2.87 |
| | 96.94 | 0.98 | 2.08 | 3.31 | 1.22 | 95.48 | 8 | 98 | 36.5 | 2.39 |
| | 87.48 | 0.65 | 11.87 | 6.2 | 1.48 | 92.32 | 8 | 98 | 32.1 | 1.15 |
| | 98.66 | 0.45 | 0.89 | 6.72 | 1.41 | 91.87 | 5 | 96 | 46.0 | 0.76 |
| | 97.32 | 0.66 | 2.01 | 7.4 | 1.53 | 91.07 | 8 | 94 | 30.5 | 1.12 |
| | 95.36 | 0.79 | 3.85 | 10.25 | 1.65 | 88.1 | 13 | 93 | 19.4 | 1.30 |
| | 94.78 | 1.16 | 4.06 | 13.89 | 1.81 | 84.3 | 9 | 95 | 10.6 | 0.65 |
| | 91.7 | 1.28 | 7.02 | 13.47 | 1.71 | 84.83 | 17 | 95 | 9.1 | 1.22 |
| | 94.26 | 1.36 | 4.38 | 43.4 | 1.76 | 54.85 | 14 | 64 | 2.8 | 0.48 |
| 16% Water | | | | | | | | | | |
| | 95.1 | 0.51 | 4.39 | 1.98 | 1.18 | 96.83 | 3 | 97 | 111.1 | 1.49 |
| | 98 | 0.56 | 1.42 | 3.73 | 1.3 | 94.97 | 7 | 98 | 61.0 | 1.88 |

TABLE VI-continued

| Polar phase MG (wt %) | Polar phase DG (wt %) | Polar phase TG (wt %) | Nonpolar phase MG (wt %) | Nonpolar phase DG (wt %) | Nonpolar phase TG (wt %) | Fat content polar phase, Wt % | Fat content less polar phase, Wt % | Selectivity MG/DG | K (mono) wt basis |
|---|---|---|---|---|---|---|---|---|---|
| 96.2 | 0.82 | 2.96 | 5.4 | 1.37 | 93.23 | 20 | 96 | 29.8 | 3.71 |
| 90.7 | 1.11 | 8.16 | 7.36 | 1.37 | 91.27 | 9 | 95 | 15.2 | 1.17 |
| 88.6 | 1.12 | 10.23 | 7.99 | 1.47 | 90.54 | 21 | 94 | 14.6 | 2.48 |
| 88.4 | 1.18 | 10.45 | 14.82 | 1.56 | 83.62 | 21 | 92 | 7.9 | 1.36 |
| 84.2 | 1.27 | 14.57 | 19.03 | 1.63 | 79.34 | 24 | 90 | 5.7 | 1.18 |
| 83 | 1.42 | 15.59 | 24.68 | 1.73 | 73.69 | 26 | 88 | 4.1 | 0.99 |
| 80.7 | 1.44 | 17.85 | 25.38 | 1.83 | 72.59 | 29 | 86 | 4.0 | 1.07 |

EXAMPLE 7
Equilibrium Distribution at Moderate Diglyceride Level

A series of experiments was run to determine the equilibrium distribution between mono-, di-, and triglycerides at moderate levels of diglyceride. Mixtures were made up using a previously extracted triglyceride oil/crude monoglyceride mixture (to provide a low level of monoglycerides and moderate level of diglycerides), distilled monoglycerides (IV 70), and aqueous ethanol. The aqueous ethanol was 23 vol % water in ethanol. The aqueous ethanol was added in an amount sufficient to give a two phase system. The samples were mixed and equilibrated at about 65° C. Aliquots were removed and the fat content determined by residual weight after evaporation in a vacuum oven at about 120° C. The evaporated samples were then derivitized and analyzed by GC to determine the monoglyceride, diglyceride, and triglyceride content. Water was determined by Karl Fisher analysis and found to be about 0–3 wt % of the less polar phase. Ethanol, determined by difference, was found to be 8–5 wt % of the less polar phase. The ethanol in the less polar phase increased with increasing monoglyceride content. Selectivity of the polar phase for monoglycerides over diglycerides and the monoglyceride extraction factor (concentrations based on weight) are shown in the attached Table VII.

roughly 70 wt % monoglyceride and 30 wt % diglyceride) with 30 grams of a polar solvent (10 g water, 20 g ethanol) and 10 grams of a triglyceride oil (fully hydrogenated soybean oil, IV less than about 5) at 70 C. and allowing the mixture to separate into two phases. Phase 1 weighed 34.7 g and had a fat content of 14.7 wt %, with composition 77.4 wt % monoglyceride, and 10.5 wt % diglyceride, and 11.9 wt % triglyceride. Phase 2 weighed 15.2 grams and had a fat content of 84.8 wt %, with a composition of 12.9 wt % monoglyceride, 17.2 wt % diglyceride, and 70 wt % triglyceride. These results indicate a selectivity for the monoglyceride over diglyceride to the polar phase of 9.8 and an extraction factor for the monoglycerides to the polar phase of 1.04, on a weight basis. The less polar phase was found to contain 2.5 wt % water, and, by difference, 12.7 wt % ethanol.

This experiment shows the general feasibility of purification of low IV monoglycerides using a low IV fat.

EXAMPLE 9
Use of Multiple Triglyceride 'Wash' Extractions in Combination with Aqueous Ethanol A four-stage batch extraction was performed by mixing 100 g crude monoglyceride (IV 70) with 200 g ethanol and 93 g water at about 70° C. and sequentially treating with 114 g aliquots of triglyceride oil (IV 40). Approximately 4–5 g

TABLE VII

| Grams Comp. #1 | Grams Comp. #2 | Grams Comp. #3 | wt % MG polar phase | wt % DG polar phase | wt % TG polar phase | wt % MG less polar phase | wt % DG less polar phase | wt % TG less polar phase | Fat content Polar phase wt % | Fat content wt %, less polar phase | Selectivity | K (mono) wt basis |
|---|---|---|---|---|---|---|---|---|---|---|---|---|
| 85.11 | 0.00 | 25.13 | 92.9 | 5.7 | 1.4 | 4.5 | 11.7 | 83.8 | 6.29 | 91.33 | 42.4 | 1.42 |
| 81.91 | 1.64 | 24.76 | 90.6 | 7.2 | 2.2 | 5.1 | 11.8 | 83.1 | 10.10 | 90.38 | 29.1 | 1.99 |
| 82.99 | 9.97 | 26.31 | 79.5 | 10.0 | 10.5 | 10.6 | 10.8 | 78.6 | 28.61 | 88.2 | 8.1 | 2.43 |
| 83.81 | 19.21 | 32.50 | 67.3 | 10.3 | 22.4 | 15.6 | 9.2 | 75.2 | 40.97 | 63.68 | 3.9 | 2.11 |
| 86.27 | 27.62 | 51.36 | 67.1 | 10.1 | 22.8 | 15.9 | 9.6 | 74.5 | 41.15 | 83.97 | 4.0 | 2.07 |
| 82.32 | 34.74 | 56.01 | 57.9 | 9.7 | 32.3 | 18.6 | 9.1 | 72.4 | 48.87 | 82.21 | 2.9 | 1.85 |
| 84.78 | 48.03 | 80.32 | 60.0 | 8.9 | 31.1 | 17.6 | 7.3 | 75 | 47.64 | 83 | 2.8 | 1.96 |

Component #1 is a mixture of 8 wt % monoglyceridea, 13 wt % diglycerides, and 79% triglycerides
Component #2 is distilled monoglycerides, used to adjust overall composition
Component #3 is aqueous ethanol, 23 vol % water in ethanol These data can be used to assist in the design of a liquid-liquid extraction process.

EXAMPLE 8
Extraction of IV 2 Crude Monoglycerides Using Triglyceride and Aqueous Ethanol A single stage separation was performed by mixing 10 g of crude glycerol monostearate (IV approximately 2, of the polar phase was removed for analysis after each extraction. Fresh triglyceride oil was used for each extraction. Samples of the polar phase and less polar phase were analyzed for water content (Karl Fisher), fat content (evaporation residue), and ethanol (by difference). The evaporated samples were then derivitized and analyzed by GC for the monoglyceride, diglyceride, and triglyceride content. Results are shown in Table VIII below.

TABLE VIII

| Phase | Water, wt % | Ethanol, wt % | Fat, wt % | Mono-glyceride, wt % | Di-glyceride, wt % | Tri-glyceride, wt % |
|---|---|---|---|---|---|---|
| Stage 1, polar | 27.1 | 59.4 | 13.5 | 83.7 | 10.7 | 5.6 |
| Stage 2, polar | 29.1 | 62.1 | 8.8 | 94.1 | 2.6 | 3.3 |
| Stage 3, polar | 25.9 | 63.6 | 10.5 | 85.8 | 1 | 13.2 |
| Stage 4, polar | 31.1 | 62.7 | 6.2 | 87.1 | 0.7 | 12.2 |
| Stage 1, less polar | 2.6 | 10.4 | 87 | 14.6 | 18.4 | 67 |
| Stage 2, less polar | 2.1 | 11.9 | 86 | 6.7 | 4.4 | 88.9 |
| Stage 3, less polar | 2.3 | 9.7 | 88 | 6.3 | 1.7 | 92 |
| Stage 4, less polar | 5.3 | 17.7 | 77 | 6.4 | 1.5 | 92.1 |

Applicants believe that additional washing stages, or a counter current extraction apparatus, could be used to reduce the diglyceride content of the polar phase to any desirable level. Applicants also believe that the triglyceride content of the polar phase can be controlled through choice of the aqueous alcohol, contacting, temperature, overall fat content, or other methods.

This example shows the progressive removal of diglycerides from monoglycerides, by washing with triglycerides.

EXAMPLE 10
Comparative Analysis of Distilled Monoglycerides

Several samples of commercially available distilled monoglycerides were analyzed by gas chromatography to determine the monoglyceride, diglyceride, and triglyceride content (excluding glycerol, free fatty acid, and other contaminants). The results, shown in Table IX below, indicate that diglycerides are the major impurity in the monoglycerides and are present at levels of greater than 2.9 wt %.

TABLE IX

| Sample ID | Monoglyceride wt % | Diglyceride wt % | Triglyceride wt % |
|---|---|---|---|
| AI90NLK | 95.01 | 3.88 | 1.11 |
| AI90AB | 96.12 | 3.13 | .075 |
| AI90PBK | 93.32 | 5.35 | 1.33 |
| AI90SBK | 96.43 | 2.91 | 0.65 |
| AI IV 70 | 96.19 | 3.63 | 0.18 |
| Danisco IV 40 | 96.99 | 3.01 | 0 |
| AI90VCK | 96.99 | 3.01 | 0 |
| AI Starplex 90 | 96.68 | 3.11 | 0.21 |

EXAMPLE 11
Washing of Raffinate to Reduce Alcohol Content

A sample of raffinate was prepared by doing a single extraction of crude monoglycerides (1000 g, IV 70) with a triglyceride mix of 500 g IV 2 soybean oil and 500 g IV 70 soybean oil and an aqueous alcohol mix of 930 g distilled water and 2000 g food grade ethanol. After equilibration at 70° C. The phases were separated and the raffinate was divided into 10 gram aliquots. The aliquots were held at 70° C. and treated as shown in Table X. The treatment reduced the ethanol content of the raffinate, as shown in Table X. Fat content was determined by evaporation residue, water by Karl Fischer, and ethanol by difference.

TABLE X

|  | Raffinate before washing | Raffinate washed 3 times, 4 ml water | Raffinate washed 2 times, 12 ml water | Raffinate washed 1 time, 25 ml water |
|---|---|---|---|---|
| Fat content, wt % | 88.3 | 96 | 96.3 | 92.4 |
| Water, wt % | 2.4 | 2 | 1.6 | 1.9 |
| Ethanol, wt % | 9.3 | 2 | 2.1 | 5.7 |

This example shown the ability to wash the raffinate by contacting with water, to reduce the alcohol content.

EXAMPLE 12
Product Recovery in a Wiped Film Evaporator

The aqueous alcohol/monoglyceride extract from extraction of crude monoglycerides of animal origin (62 wt % monoglyceride, 35 wt % diglyceride, and 3 wt % triglyceride) was pre-concentrated using a rotary evaporator to a fat content of about 44 wt %. This material was then fed at 170 g/hr. to a lab scale wiped film evaporator, Model KDL-4 from UIC, Inc., Joliet, Ill., running at an evaporator temperature of 76° C. and a pressure of 250 mm HG absolute. The bottoms product was collected and volatiles were determined by evaporation at 110° C. in flowing nitrogen. The residual volatiles, water and ethanol, were less than 0.4 wt %.

EXAMPLE 13
GC Analytical Procedure

Fat compositions can be determined by any suitable method, for example gas chromatography. A preferred method is to evaporate the samples at approximately 110° C. in flowing nitrogen, or under vacuum, to remove water and alcohol. Approximately 0.4 g of sample is then dissolved in 400 microliter of chloroform and derivitized by adding 400 microliter of pyridine and 200 microliter of BSTFA solution from Regis Technologies, Inc., Morton Grove, Ill. (BSTFA is Bis(trimethylsilyl)trifluoroacetamide). The sample is then analyzed using a Hewlett Packard Model 5890 using a 1 meter capillary column, Model DB5HT from J&W. The sample is prepared for GC injection by diluting 10 microliters of the derivitized solution with 1.5 ml of dry chloroform prior to injection. The area percent figures are converted to weight percent for the monoglycerides, diglycerides, and triglycerides using relative response factors determined from appropriate standards. The totals are normalized to 100% for the combined mono-, di-, and triglycerides.

EXAMPLE 14
Effective Polar Phase Composition and Extraction Coefficient; Emulsion Formation A mixture of fats was prepared from 900 g IV 70 crude monoglyceride and 600 g of partially hydrogenated vegetable oil. An initial aqueous extraction phase was prepared from 360 grams ethanol and 90 grams water. This solution was contacted with 450 g of the fat mixture, which had been melted and was held at 63–70 C. The combined mixture was stirred at 1000 rpm for 10 minutes, then allowed to settle for 30 minutes. After settling, a small sample was taken of each phase and analyzed for fat content and composition. After each test, additional fat mixture and additional water was added, keeping the total amount of fat roughly equal to the combined weight of water plus ethanol, while adjusting the water content of the water/ethanol phase higher. In the table below (Table XI), the calculated water content is based on the nominal water plus ethanol content. When the water content was 36 wt. % or less, the aqueous phase was on top; around 40 wt. % water, the aqueous phase and oil phase had similar density and did not phase separate; at 44 wt. % water or higher, the aqueous phase was on the bottom; and at 52 wt. % water or higher, the oil phase was cloudy and the compositional analysis seemed to indicate an emulsion had formed. Fat content is reported as weight % fat based on total phase weight, MG, DG and TG are the weight percent of fat which is monoglyceride, diglyceride or triglyceride, respectively.

extraction train, consisting of about 4 mixer/settler vessels. This extraction train would be known as the primary extraction train. To the other end of the extraction train would be charged 14,630 lb./hr. of an aqueous alcohol extractant, consisting of 10,850 lb./hr. of ethanol and 3,780 lb./hr. water. The raffinate phase, following extraction, would contain about 2115 lb./hr. triglyceride, 1330 lb./hr. diglyceride, 20 lb./hr. monoglyceride, 80 lb./hr. water, and 350 lb./hr. ethanol. The raffinate stream would be contacted countercurrently with 700 lb./hr. of water, to form an aqueous phase with 700 lb./hr. water and 270 lb./hr. of ethanol, which would be used as a portion of the aqueous alcohol extractant composition. The raffinate would then be vacuum stripped to remove ethanol and water and would be used as a feedstock to a monoglyceride production reactor.

The extractant phase, following the extraction train, would contain approximately 10,850 lb./hr. ethanol, 3,780 lb./hr. water, 2,400 lb./hr. monoglyceride, 350 lb./hr. diglyceride, and 200 lb./hr. triglyceride. This phase would be fed to one end of a countercurrent extraction train, containing another 4 mixer/settler stages. This extraction train would be used to "wash" the diglycerides from the aqueous alcohol extractant phase to further purify the monoglycerides. To the other end of the train would be fed about 2065 lb./hr. of triglyceride. After extraction, the triglyceride rich

TABLE XI

| Wt % | Polar Phase | | | | Less-polar phase | | | | | | |
|---|---|---|---|---|---|---|---|---|---|---|---|
| Water | % fat | MG | DG | TG | % fat | MG | DG | TG | $K_{mono}$ | $K_{di}$ | $K_{tri}$ |
| 20 | 34 | 60.1 | 18.5 | 21.4 | 74 | 18.2 | 18.3 | 63.4 | 1.52 | 0.46 | 0.16 |
| 24 | 32 | 65.7 | 17.1 | 17.3 | 74 | 19.1 | 19.2 | 61.8 | 1.49 | 0.39 | 0.12 |
| 28 | 29 | 69.7 | 15.8 | 14.4 | 78 | 19.5 | 19.8 | 60.7 | 1.33 | 0.3 | 0.09 |
| 32 | 27 | 72.6 | 14.6 | 12.8 | 78 | 20.8 | 20.2 | 59 | 1.21 | 0.25 | 0.08 |
| 36 | 25 | 70.2 | 13.9 | 15.8 | 76 | 23.7 | 20.2 | 56.2 | 0.97 | 0.23 | 0.09 |
| 44 | 10 | 70.4 | 11.3 | 18.3 | 68 | 33.2 | 19.5 | 47.3 | 0.31 | 0.09 | 0.06 |
| 48 | 4 | 74.8 | 8.7 | 16.5 | 73 | 34.7 | 19.6 | 45.7 | 0.12 | 0.02 | 0.02 |
| 52 | 2 | 59 | 12 | 29 | 75 | 34.1 | 18.2 | 47.7 | 0.05 | 0.02 | 0.02 |
| 56 | 2 | 50.6 | 14.4 | 35 | 79 | 35.2 | 19.2 | 45.7 | 0.04 | 0.02 | 0.02 |
| 62 | 2 | 40 | 17.2 | 42.7 | 81 | 35.2 | 19.3 | 45.5 | 0.03 | 0.02 | 0.02 |
| 67 | 2 | 36.8 | 18.2 | 44.9 | 79 | 34.5 | 18.6 | 46.9 | 0.03 | 0.02 | 0.02 |

It is noted that the fat content of the polar phase, $K_{mono}$, and $K_{di}$ drop rapidly, starting at a nominal water content of 36 wt. %. At those conditions, it should be possible to wash the system and remove water soluble impurities without extracting a significant portion of the monoglycerides.

A Hypothetical Commercial System

A commercial plant, with a capacity of about 20 million pounds of purified monoglyceride per year, could theoretically be set up with the following flow rates. A triglyceride rich stream, with a flow rate of about 2165 lb./hr. triglyceride, and other components as described in the wash extraction section, would be mixed with a crude monoglyceride stream which has a flow rate of 3900 lb./hr, consisting of 2400 lb./hr. of monoglyceride, 1350 lb./hr. diglyceride, and 150 lb./hr. of triglyceride. The crude monogloycerides would be prepared by the reaction of diglycerides, triglycerides, and glycerin using a catalyst, such as NaOH or other bases. After the reaction, the catalyst would be neutralized and removed and the crude monoglycerides cooled. Excess glycerin would be decanted off and an evaporator would be used to further strip glycerin from the product. The combined stream (crude monoglycerides and triglyceride rich stream) would be charged to one end of a countercurrent stream would have a flow rate of about 2165 lb./hr. of triglyceride, 330 lb./hr. of diglyceride, 20 lb./hr. of monoglyceride, 80 lb./hr. water, and 350 lb./hr. ethanol. It would preferably be used as the triglyceride rich stream feed to the primary extraction train, described above. The extractant phase, following the wash extraction stage, would have a flow rate of about 10,500 lb./hr. ethanol, 3700 lb./hr. water, 2380 lb./hr. monoglyceride, 20 lb./hr. diglyceride and 100 lb./hr. triglyceride.

The purified monoglycerides would be removed from the extractant stream. For example, a multiple stage evaporator, perhaps followed by a wiped film evaporator, would be used to remove the ethanol and water to produce a stream of molten monoglycerides, containing approximately 2380 lb./hr. monoglyceride, 20 lb./hr. diglyceride, and 100 lb./hr. triglyceride.

Use of Purified Monoglycerides or Purified PGME

Purified monoesters can be used to prepare a liquid shortening, suitable for use in bread, cake batter, pizza dough, and other applications. The liquid shortening would consist of up to about 12 wt % purified monoester, about 2–8 wt % of a solid fat with IV less than about 6, and the remainder would primarily be a liquid oil, such as partially hydrogenated vegetable oil with an IV of about 90 to 140.

Purified monoesters can also be used to prepare a plastic shortening, suitable for use in cake mixes, and would contain about 2–14 wt % of the purified monoester (typically PGME). For bread shortenings, the level of monoester would be higher, amounting to about 6–20 wt % of the shortening, to achieve a total level in the bread of about 0.2–2.5 wt % monoester.

Purified monoglycerides can also be added directly to bakery products. Typically the monoglyceride would be added at a rate of 0.2–0.5 wt %, dry, based on flour. The monoglyceride would typically be hydrated prior to use.

Purified monoglycerides, typically with IV less than about 5, could also be added directly to starch-based foods and dried potato products. The use level would typically be 0.1–1.5 wt %.

Purified PGME, with an IV less than about 5, can also be used in whipped toppings, with a use level typically of 0.5–2 wt %, and in powdered toppings at levels of 5–10 wt %.

The purified monoglycerides are also suitable for use in making margarine. For example, a stick margarine or whipped hard margarine can be made using about 0.1–0.5 wt % of purified monoglyceride (IV less than about 5), about 80 wt % vegetable fat (may be partially hydrogenated), about 17% water or milk, and salt, vitamins, flavor, color, antioxidants, other emulsifiers, etc. A soft margarine (tub margarine) could be made in a similar manner, but the monoglyceride level would preferably be increased slightly and the IV of the monoglyceride would typically be about 30–70. The vegetable fat would be largely replaced with a partially hydrogenated vegetable oil to provide the desired degree of softness. A liquid margarine would use a monoglyceride with an IV of 70–125 and would replace the vegetable fat with a liquid vegetable oil with just a few percent of hard fat dispersed in it (a liquid shortening).

Diet table spreads can be made using 40–75 wt % of a vegetable fat (may be partially hydrogenated), 23–58 wt % water, 0.5–1.5 wt % purified monoglyceride (IV typically 70–125), and salt, vitamins, flavor, color, antioxidants, other emulsifiers, etc. As the amount of fat is reduced the amount of monoglyceride is increased. For spreads with less than 40% fat, the monoglyceride content would typically be 1–2 wt %, and for fat-free spreads the monoglyceride content would typically be about 2–4 wt %.

The purified monoesters, when combined with other additives, are also suitable for ice cream production.

X. Some Variations

It is anticipated that in some applications variations of the techniques described herein will be desirable. For example, if the triglycerides content of the polar phase of leaving the washing step, for example in line 66, FIG. 1, is undesirably high, steps can be taken to lower its content before the monoglycerides are purified or isolated. This can be done, for example, by increasing the water content, rendering the triglycerides less soluble in the polar phase. In addition, a non-polar solvent, such as a hydrocarbon solvent, could be used to facilitate this. It is noted that in general it is preferred to avoid hydrocarbon solvents in systems according to the present invention but they may find some use in such instances.

As an alternative to the approach described in the previous paragraph, one could include hydrocarbon solvents in the triglycerides feed in line 65, FIG. 1, going into the washing step 60. Generally, it is anticipated that if this is practiced, this system would involve less than 20% by weight hydrocarbon solvent, and typically 10% by weight or less, based on total weight of triglycerides plus hydrocarbon, i.e., non-polar solvent. It is foreseen that the addition of hydrocarbon solvents will not be preferred, since steps would need to be taken to handle their removal. However, they may be useful to facilitate some liquid/liquid extractions in systems according to the present invention.

Also, in some options one may wish to add water or alcohol to the polar phase as it leaves the extraction step and prior to the washing step, for example, addition to line 55, FIG. 1. This would be done in order to modify the polarity of the phase, thereby affecting the solubility of diglycerides and/or triglycerides therein, during the washing step.

It is also noted that in some systems mixed alcohols may be desirable, as the alcohol solvent in the alcohol phase. This might be usable to fine tune the selectivities in some systems, for example.

In some systems, it may be desirable to conduct both the primary extraction and the follow up washing in the same multi-stage extraction equipment. In such systems, the crude monoglyceride feed would occur at an intermediate location.

What is claimed is:

1. A process for producing a crude monoglycerides mixture and for purification of monoglycerides, the process comprising steps of:
   (a) reacting a glycerol feed and a triglyceride feed in the presence of a catalyst to form a crude monoglycerides mixture;
   (b) extracting said crude monoglycerides mixture by liquid-liquid extraction to provide:
      (i) an extractant stream comprising purified monoglycerides; and
      (ii) a raffinate stream comprising triglycerides; and
   (c) recovering triglycerides from said raffinate stream to provide recovered triglycerides and adding said recovered triglycerides with said triglyceride feed.

2. A process according to claim 1, wherein the triglyceride feed comprises an oil selected from the group consisting of: palm oil, sunflower oil, canola oil, soybean oil, and mixtures thereof.

3. A process according to claim 1, wherein the catalyst comprises a base catalyst.

4. A process according to claim 3, further comprising steps of:
   (a) neutralizing the base catalyst after formation of the crude monoglycerides mixture; and
   (b) removing a glycerol phase from said crude monoglycerides mixture prior to said step of extracting.

5. A process according to claim 1, wherein the step of extracting takes place in a counter-current extractor.

6. A process according to claim 5, wherein said step of extracting comprises feeding said crude monoglycerides mixture and alcohol/water mixture to the extractor.

7. A process according to claim 1, wherein said extractant stream comprises monoglycerides, alcohol and water.

8. A process according to claim 1, further comprising a step of:
   (a) extracting said extractant stream with a triglycerides phase by liquid—liquid extraction to provide:
      (i) a purified monoglycerides phase; and
      (ii) a triglycerides phase.

9. A process according to claim 8, wherein said triglycerides phase from step (a)(ii) is combined with said crude monoglycerides mixture.

10. A process according to claim 1, wherein said triglyceride feed comprises, at least in part, triglycerides from said raffinate stream.

11. A process for purification of monoglycerides, the process comprising steps of:
(a) providing a crude monoglycerides mixture comprising monoglycerides, diglycerides, and triglycerides;
(b) adding triglycerides to said crude monoglycerides mixture; and
(c) extracting said crude monoglycerides mixture containing added triglycerides by liquid-liquid extraction to provide:
   (i) an extractant stream comprising purified monoglycerides; and
   (ii) a raffinate stream comprising triglycerides.

12. A process according to claim 11, wherein said step of extracting said crude monoglycerides mixture containing added triglycerides by liquid—liquid extraction comprises extracting with a stream comprising alcohol and water.

13. A process according to claim 11, further comprising a step of:
(a) adding water to said raffinate stream to provide:
   (i) an organic phase comprising triglycerides; and
   (ii) a water phase comprising alcohol.

* * * * *